United States Patent
Eiznhamer et al.

(10) Patent No.: US 12,097,202 B2
(45) Date of Patent: Sep. 24, 2024

(54) METHODS OF ADMINISTERING BELUMOSUDIL FOR TREATMENT OF CHRONIC GRAFT VERSUS HOST DISEASE

(71) Applicant: Kadmon Corporation, LLC, Bridgewater, NJ (US)

(72) Inventors: David Eiznhamer, Cambridge, MA (US); Heidi Krenz, Cambridge, MA (US)

(73) Assignee: Kadmon Corporation, LLC, Bridgewater, NJ (US)

( * ) Notice: Subject to any disclaimer, the term of this patent is extended or adjusted under 35 U.S.C. 154(b) by 0 days.

(21) Appl. No.: 18/105,285

(22) Filed: Feb. 3, 2023

(65) Prior Publication Data
US 2024/0024321 A1 Jan. 25, 2024

Related U.S. Application Data

(63) Continuation of application No. PCT/US2022/037207, filed on Jul. 14, 2022.

(51) Int. Cl.
*A61K 31/517* (2006.01)
*A61K 9/20* (2006.01)
*A61P 37/06* (2006.01)

(52) U.S. Cl.
CPC .......... *A61K 31/517* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61P 37/06* (2018.01)

(58) Field of Classification Search
CPC .. A61K 31/517; A61K 9/2009; A61K 9/2013; A61K 9/2027; A61K 9/2031; A61K 9/2054; A61P 37/06
See application file for complete search history.

(56) References Cited

U.S. PATENT DOCUMENTS

| | | |
|---|---|---|
| 8,357,693 B2 | 1/2013 | Bartolozzi et al. |
| 9,815,820 B2 | 11/2017 | Poyurovsky et al. |
| 10,183,931 B2 | 1/2019 | Poyurovsky et al. |
| 10,696,660 B2 | 6/2020 | Poyurovsky et al. |

OTHER PUBLICATIONS

Anonymous. Drugs [online]; 2022; published Jun. 21, 2022; downloaded from <URL https://www.drugs.com/dosage/belumosudil.html#:~:text=Other Adverse REACTIONS%3A Permanently discontinue therapy. > on Aug. 10, 2023; 3 pages. (Year: 2022).*
Anonymous. Drugs [online]; 2021; downloaded from <URL https://www.drugs.com/rezurock.html > on Aug. 10, 2023; 4 pages. (Year: 2021).*
Anonymous: "Application No. 214783Orig1s000: Multi-Discipline Review Summary Review Clinical Review Non-Clinical Review Statistical Review Clinical Pharmacology Review", Jul. 16, 2021, retrieved from the internet: https://www.accessdata.fda.gov/drugsatfda_docs/nda/2021/214783Orig1s000MultidisciplineR.pdf [retrieved on Feb. 20, 2023], 325 pages.
Anonymous: "Belumosudil Pregnancy and Breastfeeding Warnings", Jun. 21, 2022, retrieved from the internet: https://www.drugs.com/pregnancy/belumosudil.html on Feb. 17, 2023, 2 pages.
Anonymous: Highlights of Prescribing Information: Rezurock (TM) (belumosudil) tablets, for oral use Initial U.S. Appoval: 2021, retrieved from the internet: https://www.rezurockhcp.com/full-prescribing-information.pdf [retrieved on Feb. 20, 2023], 16 pages.
Bachier, Carlos R. et al., "Epidemiology and Real-World Treatment of Chronic Graft-Versus-Host Disease Post Allogeneic Hematopoietic Cell Transplantation: A US Claims Analysis", Blood (2019) 134 (Supplement_1): 2109.
Carpenter, Paul A. et al., "A phase II/III randomized, multicenter trial of prednisone/sirolimus versus prednisone/sirolimus/calcineurin inhibitor for the treatment of chronic graft-versus-host disease: BMT CTN 0801," Haematologica 2018, 103(11): 1915-1924.
Chen, Jiezhong et al., "Roles of rifampicin in drug-drug interations: underlying molecular mechanisms involving the nuclear pregnane X receptor", Ann Clin Microbiol Antimicrob, 2006, 5:3, 11 pages.
Hardin, Thomas C. et al., "Pharmacokinetics of Itraconazole following Oral Administration to Normal Volunteers", Antimicrobial Agents and Chemotherapy, Sep. 1988, 32(9), 1310-1313.
Kantola, Teemu et al., "Effect of itraconazole on the pharmacokinetics of atorvastatin", Clinical Pharmacology & Therapeutics, 64 (1), 1998, 58-65.
Lebrun-Vignes, B. et al., "Effect of itraconazole on the pharmacokinetics of prednisolone and methylprednisolone and cortisol secretion in healthy subjects", Br J Clin Pharmacol, 51, 2001, 443-450.
Lee, Stephanie J. et al., "Development and Validation of a Scale to Measure Symptoms of Chronic Graft-versus-Host Disease", Biology of Blood and Marrow Transplantation 8:444-452 (2002).
Lee, Stephanie J. et al., "Success of Immunosuppressive Treatments in Patients with Chronic Graft-versus-Host Disease", Biol Blood Marrow Transplant 24 (2018) 555-562.
Martin, Paul J. et al., "An endpoint associated with clinical benefit after initial treatment of chronic graft-versus-host disease", Blood, 2017, 130:3, 360-367.
PCT International Search Report and Written Opinion for PCT/US2022/037207, mailed on Mar. 2, 2023, 10 pages.
PCT International Search Report and Written Opinion from PCT/US2022/037200, mailed Mar. 2, 2023, 10 pages.

(Continued)

*Primary Examiner* — David Browe
(74) *Attorney, Agent, or Firm* — McNeill PLLC

(57) ABSTRACT

The present disclosure provides methods of administering belumosudil mesylate salt to patients with chronic graft-versus-host disease (cGVHD), wherein the methods include identifying adverse reactions in the patients, such as an infection, and modifying the administration based on the results of such identification, such as by ceasing administration when the infection is a Grade 3 or Grade 4 level infection.

6 Claims, 14 Drawing Sheets

(56) References Cited

OTHER PUBLICATIONS

PCT International Search Report from PCT/US2022/037192, mailed on Mar. 2, 2023, 10 pages.
PCT International Search Report from PCT/US2022/037210, mailed on Mar. 2, 2023, 10 pages.
Przepiorka, Donna et al., "FDA Approval Summary: Belumosudil for Adult and Pediatric Patients 12 Years and Older with Chronic GVHD After Two or More Prior Lines of Systemic Therapy", Clin Cancer Res. Jun. 13, 2022; 28(12): 2488-2492.
Schueller, Olivier et al., "A Phase 1 Pharmacokinetic Drug Interaction Study of Belumosudil Coadministered With CYP3A4 Inhibitors and Inducers and Proton Pump Inhibitors", Clinical Pharmacology in Drug Development, 11(7), Jul. 2022, 795-806.
Schueller, Olivier et al., "Absolute Bioavailability, Mass Balance, and Metabolic Profiling Assessment of [I4C]-Belumosudil in Healthy Men: A Phase I, Open-Label, 2-Part Study", Clinical Pharmacology in Drug Development, 2022, 11(7) 786-794.
Schueller, Olivier et al., "Phase I Studies to Evaluate the Food Effect and Relative Bioavailability of Tablet and Capsule Formulations of Belumosudil in Healthy Adult Subjects", Clinical Pharmacology in Drug Development, vol. 11, No. 7, Mar. 2, 2022, pp. 807-814.
Waller, Edmund K. et al., "Ibrutinib for Chronic Graft-versus-Host Disease After Failure of Prior Therapy: 1-Year Update of a Phase 1b/2 Study", Biol Blood Marrow Transplant 25 (2019) 2002-2007.
U.S. Department of Health and Human Services, Common Terminology Criteria for Adverse Events (CTCAE), Version 4.03, Jun. 14, 2010, 80 pages.
U.S. Department of Health and Human Services, Common Terminology Criteria for Adverse Events (CTCAE), Version 5.0, Nov. 27, 2017, 155 pages.

* cited by examiner

| | Responder | GSR | Eye | Skin | Mouth | Joints and fascia | Lung | Upper GI | Esophagus | Lower GI | Liver |
|---|---|---|---|---|---|---|---|---|---|---|---|
| Cohort 1, 200 mg Once Daily | Y | PR | St | CR | PR | St | | | | | |
| | Y | PR | St | St | St | PR | | | | | |
| | Y | PR | PR | | CR | | | | | | |
| | Y | PR | PR | | | St | | CR | | | |
| | Y | PR | CR | | CR | | | CR | | CR | |
| | Y | PR | St | CR | CR | | | St | | St | |
| | Y | PR | CR | St | CR | PR | | | | | |
| | Y | St | St | St | St | PR | | | | | |
| | Y | PR | St | PR | PR | PR | St | CR | | | |
| | Y | PR | St | St | St | PR | St | | | | |
| | Y | St | CR | | | St | | | | | |
| | N | PR | St | P | St | | | | | | |
| | N | | St | P | St | P | | | | | |
| | N | St | St | St | PR | PR | | | | | St |
| | N | St | | P | St | St | | | | | |
| | N | St | St | St | St | | St | St | | | |
| | N | St | St | St | St | St | | | | | St |
| Cohort 2, 200 mg Twice a Day | Y | PR | PR | | | PR | | | | | |
| | Y | PR | St | St | St | PR | | CR | | | |
| | Y | PR | St | | CR | | | | | | |
| | Y | PR | | St | CR | PR | | CR | | | St |
| | Y | PR | CR | CR | CR | St | | St | | CR | St |
| | Y | PR | PR | St | | St | | CR | St | | |
| | Y | St | St | St | PR | St | | | | | |
| | Y | St | | St | St | St | | | | | CR |
| | Y | PR | St | | St | | St | St | | | |
| | Y | PR | PR | PR | St | PR | | | | | St |
| | Y | St | St | St | St | PR | | | | | St |
| | N | P | | P | St | New | | | | | |
| | N | St | St | St | CR | P | St | CR | | | CR |
| | N | St | | St | St | St | | St | St | St | |
| | N | St | St | St | St | St | | | | | |
| | N | St | | | | St | | | | | |
| Cohort 3, 400 mg Once Daily | Y | PR | St | CR | PR | | | | | | |
| | Y | PR | | St | | St | | | | | |
| | Y | PR | St | St | CR | PR | PR | | | | |
| | Y | St | | St | St | CR | | | CR | | |
| | Y | St | St | St | St | | PR | | | | |
| | Y | PR | St | St | St | PR | St | St | | | |
| | Y | PR | PR | | St | | St | | | St | |
| | Y | St | St | St | CR | PR | St | | | St | |
| | Y | PR | St | PR | CR | St | | | CR | | |
| | Y | PR | PR | | | PR | | St | | | |
| | Y | PR | PR | | St | | St | | | | |
| | Y | PR | CR | St | CR | PR | | | | | |
| | Y | PR | St | St | | CR | | | CR | | |
| | N | St | St | St | P | St | | | | | |
| | N | St | St | St | St | | | | | | |
| | N | St | | St | | St | | | | | |
| | N | St | St | | | | St | St | St | | |
| | N | St | St | | | St | St | | | | |

| | Responder | GSR | Eye | Skin | Mouth | Joints and fascia | Lung | Upper GI | Esophagus | Lower GI | Liver |
|---|---|---|---|---|---|---|---|---|---|---|---|
| Cohort 1, 200 mg Once Daily | N | St | | St | PR | P$^a$ | | | | | |
| | N | PR | St | St | | PR | | | | | |
| | N | PR | PR | | CR | | | | | | |
| | N | St | St | | | | P | | CR | | |
| | N | St | St | | St | | | CR | | P | |
| | N | PR | P | PR | Pr | | | St | | St | |
| | N | PR | CR | St | CR | PR | | | | | |
| | N | St | St | St | St | PR | | | | | |
| | N | PR | St | St | St | PR | St | CR | | | |
| | N | St | St | St | St | St | | | | | |
| | N | St | CR | | | St | | | | | |
| | Y | PR | St | P | St | | | | | | |
| | Y | | St | P | St | P$^a$ | | | | | |
| | Y | St | P | St | PR | PR | | | | | St |
| | Y | St | | P | St | St | | | | | |
| | Y | St | St | St | St | St | | | St | | |
| | Y | St | St | St | P | St | | | | | St |
| Cohort 2, 200 mg Twice a Day | N | PR | PR | | | P | | | | | |
| | N | St | St | St | St | P$^a$ | | CR | | | |
| | N | PR | St | | PR | | | | | | |
| | N | PR | | P | CR | P$^a$ | | St | | | |
| | N | PR | St | PR | St | | | | | CR | New |
| | N | PR | PR | St | | P$^a$ | | CR | | | |
| | N | St | P | St | PR | St | | | | | |
| | N | P | New | St | St | St | | | | | |
| | N | St | St | | | | St | | | | |
| | N | St | PR | St | St | PR | | | | | St |
| | N | St | St | St | St | PR | | | | | St |
| | Y | P | | P | St | New | | | | | |
| | Y | St | St | St | PR | P | P | CR | | | CR |
| | Y | St | | St | St | St | | | | | |
| | Y | St | St | St | St | St | | | | | |
| | Y | St | | | | St | | | | | |
| Cohort 3, 400 mg Once Daily | N | PR | St | CR | PR | | | | | | |
| | N | St | | St | | P$^a$ | | | | | |
| | N | PR | P | St | PR | St | PR | | | | |
| | N | St | | St | St | CR | | | CR | | St |
| | N | St | St | St | St | | St | | | | |
| | N | PR | St | St | P | | PR | St | St | St | |
| | N | St | St | | | | St | | | | |
| | N | St | P | P | CR | P$^a$ | P | | | St | |
| | N | PR | St | PR | St | St | | | | CR | |
| | N | St | PR | | | P | | | | New | |
| | N | St | St | | St | | St | | | | |
| | N | PR | St | St | CR | PR | | | | | |
| | N | PR | St | | | P | | | CR | | |
| | Y | St | St | St | P | St | | | | | |
| | Y | St | St | St | P | | | | | | |
| | Y | St | | St | | St | | | | | |
| | Y | St | St | | | | St | | | | |
| | Y | St | St | | | | | | | P | |

New - New onset cGVHD in organ  
P - Progression  
St - Stable cGVHD  
PR - Partial response  
CR - Complete response  
P$^a$ - Progression in joints and facia based in P-ROM reduction of 1 point

*Fig. 3B*

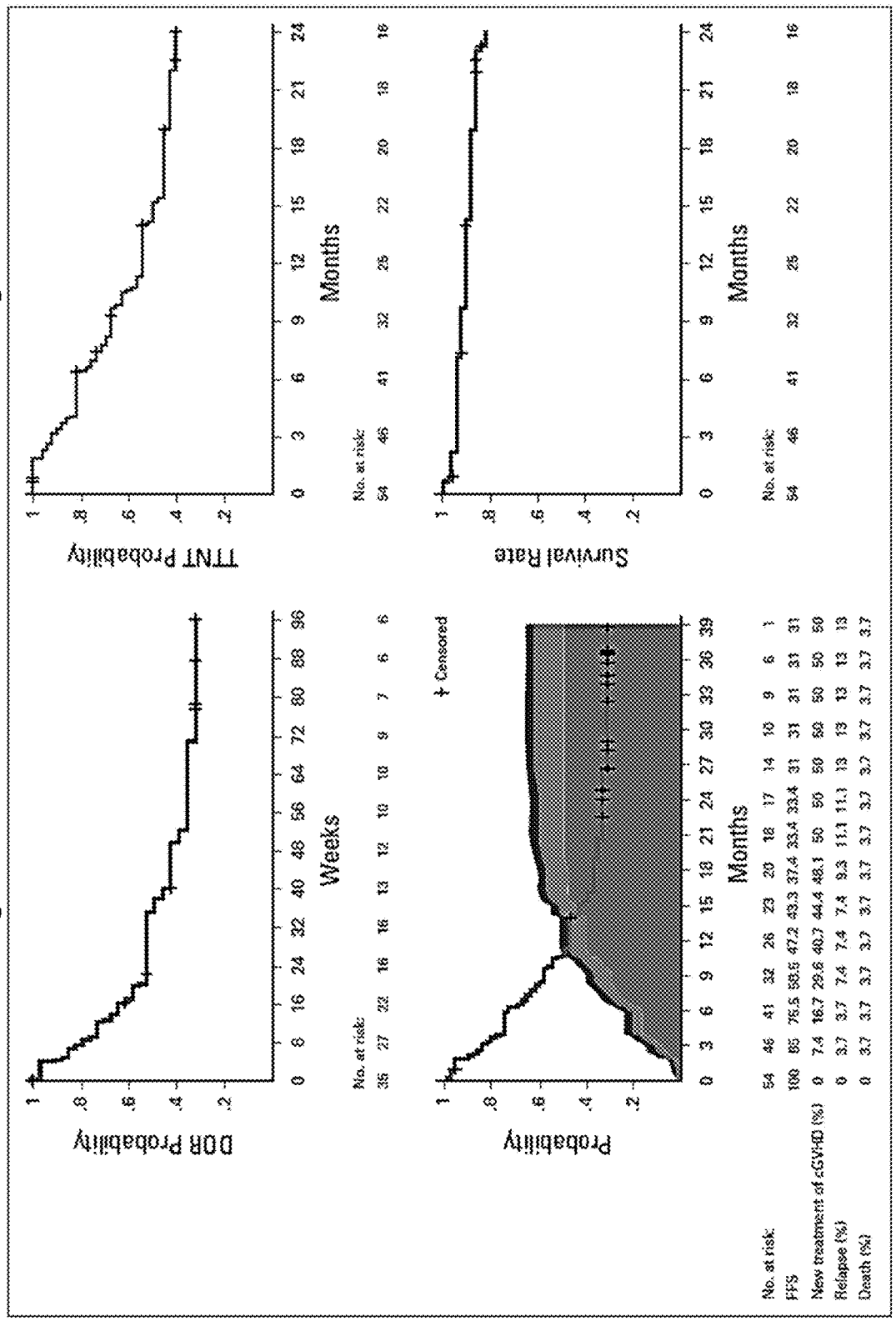

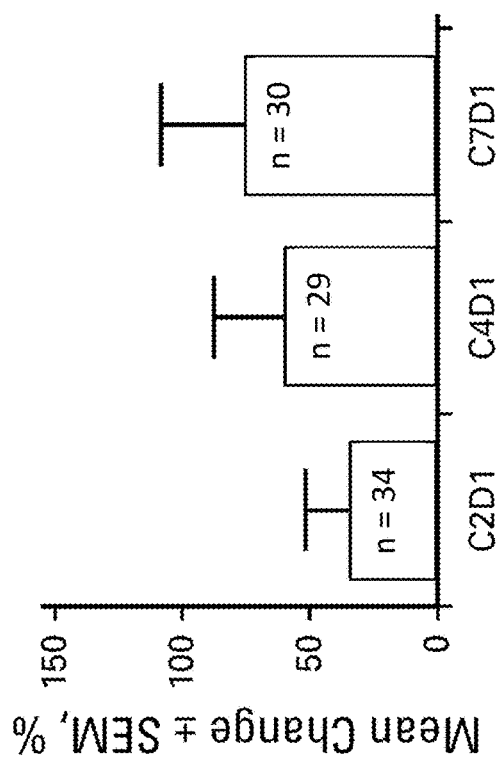
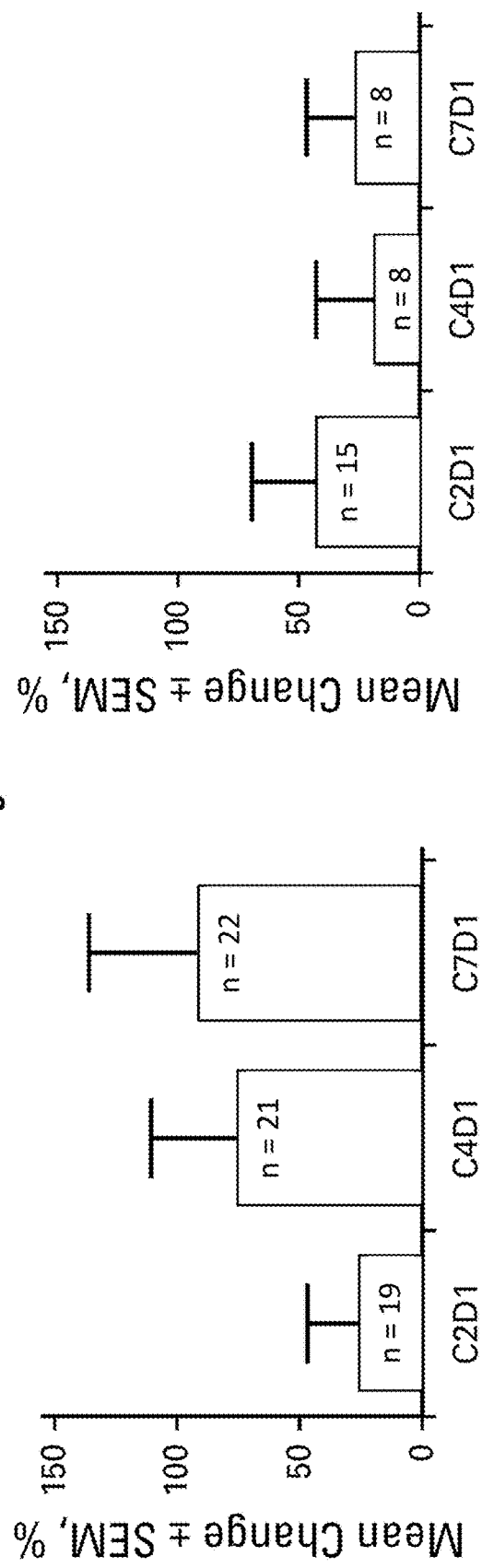
Fig. 6A
Fig. 6B
Fig. 6C

METHODS OF ADMINISTERING BELUMOSUDIL FOR TREATMENT OF CHRONIC GRAFT VERSUS HOST DISEASE

CROSS-REFERENCE TO RELATED APPLICATIONS

This application is a continuation under 35 U.S.C. § 111(a) of International Patent Application No. PCT/US2022/037207, filed on Jul. 14, 2022, which is incorporated herein by reference in its entirety.

TECHNICAL FIELD

The present disclosure relates to methods of administering belumosudil mesylate (REZUROCK™) to patients for the treatment of chronic graft-versus-host disease (cGVHD).

BACKGROUND

Chronic graft-versus-host disease (cGVHD) is an immune-mediated inflammatory and fibrotic disorder. It is a potential, serious complication following solid organ transplant and allogeneic hematopoietic cell transplant (alloHCT). cGVHD affects up to 70% of all alloHCT recipients, with an incidence of 20%-50% in children. It is the leading cause of non-relapse mortality beyond 2 years after alloHCT. The estimated prevalence of cGVHD is 14,000 patients in the United States (as of 2016). (Bachier C R et al: *Epidemiology and real-world treatment of chronic graft-versus-host disease post allogeneic hematopoietic cell transplantation: A US claims analysis*. Presented at ASH 2019, Orlando, FL, Dec. 7-10, 2019) ("Bachier et al.")

Patients with cGVHD have substantial impairment in quality of life (QOL) as assessed by the Lee Symptom Scale (LSS), which measures the effect of cGVHD on patients' functioning and well-being. It is reported that only one third of patients who have cGVHD and start systemic treatment will be alive, in remission and off immunosuppressive therapy by 5 years. (Lee S J et al: *Success of immunosuppressive treatments in patients with chronic graft-versus-host disease*. Biol Blood Marrow Transpl 24:555-562, 2018) ("Lee et al.").

The pathophysiology of cGVHD can be separated into three phases: early inflammation because of tissue injury, a dysregulated adaptive immune system, and chronic inflammation and aberrant tissue repair with fibrosis.

First-line therapy for National Institutes of Health (NIH)—defined moderate to severe chronic graft-versus-host disease (cGVHD) is corticosteroids alone or in combination with sirolimus or a calcineurin inhibitor. However, up to 70% of patients require additional lines of therapy. (Bachier C R et al). Furthermore, the long-term use of corticosteroids is associated with significant side effects. (Lee et al).

Management of cGVHD continues to evolve with the advent of targeted therapies. cGVHD is characterized by an overproduction of proinflammatory cytokines IL-21 and IL-17, as well as overactivation of T follicular helper cells and B cells, which in turn leads to overproduction antibodies.

In 2017, the US Food and Drug Administration approved ibrutinib, a Bruton's Tyr kinase inhibitor, for the treatment of adults with cGVHD after failure of one or more 1 systemic lines of therapy. In patients with cGVHD who were required to have either >25% body surface area erythematous rash or an NIH mouth score of >4, a study with ibrutinib reported an overall response rate (ORR) of 67% and a discontinuation rate because of treatment-emergent adverse events (TEAEs) of 43%. (Waller E K, et al: *Ibrutinib for chronic graft-versus-host disease after failure of prior therapy: 1-Year update of a phase 1b/2 study*. Biol Blood Marrow Transpl 25:2002-2007, 2019).

There remains an opportunity to study other treatment options for patients with cGVHD, including those who have failed >1 lines of therapy.

SUMMARY

The present disclosure provides methods of administering belumosudil mesylate (REZUROCK™) to patients for treatment of cGVHD.

In one embodiment, the present disclosure provides for use of 2-{3-[4-(1H-indazol-5-ylamino)-2-quinazolinyl]phenoxy}-N-(propan-2-yl) acetamide, or a pharmaceutically acceptable salt thereof (Compound), and/or belumosudil mesylate, in a patient who experiences one or more treatment-related, adverse reactions while receiving a clinically-recommended dose of the Compound comprising: ceasing administration of the Compound to the patient if the patient experiences at least one adverse reaction at a Grade 3 level or higher; and resuming administration of the Compound at a clinically recommended dose for the patient if the at least one adverse reaction did not rise to a Grade 4 level and the patient recovered to a Grade 1 level or less after treatment was ceased.

In one embodiment, the present disclosure provides for the use of Compound, or belumosudil mesylate, and/or methods of treating a subject for cGVHD, comprising the steps of: administering the Compound to a patient at the clinically recommended dose for the patient; monitoring the patient for adverse reactions; ceasing administration of the Compound to the patient if the patient experiences at least one adverse reaction at a Grade 3 level; and resuming administration of the Compound to the patient when the patient's at least one adverse reaction has recovered to Grade 1 or less.

In another embodiment, the present disclosure provides for permanently ceasing administration of the Compound to the patient if the patient experiences at least one adverse reaction at a Grade 4 level.

The present disclosure and further embodiments can be understood more fully by reference to the detailed description and examples, which are intended to exemplify non-limiting embodiments.

BRIEF DESCRIPTION OF THE DRAWINGS

FIG. 3B is a response and progression heat map for all patients in the safety population. (A) Best response by organ. (B) Organ responses at time of progression or end of study. Of 11 patients with progression in joints, seven had a reduction in P-ROM of just one unit.

FIG. 5A describes durability of response to belumosudil in patients with cGVHD. Kaplan-Meier curves of estimated DOR for responders FIG. 5B describes durability of response to belumosudil in patients with cGVHD. Kaplan-Meier curves of estimated time to next cGVHD systemic treatment (TTNT) in the safety population.

FIG. 5C describes durability of response to belumosudil in patients with cGVHD. Kaplan-Meier curves of estimated FFS in the safety population (including reasons for failure).

FIG. 5D describes durability of response to belumosudil in patients with cGVHD. Kaplan-Meier curves of estimated overall survival in the safety population.

FIG. 6A describes changes in percentage of CD41 Tregs following treatment with belumosudil compared with baseline for Tregs (regulatory T cells all). Predose peripheral blood samples were collected on C1D1 (cycle 1 day 1), C2D1 (cycle 2 day 1), C4D1 (cycle 4 day 1), C7D1 (cycle 7 day 1), and end-of-treatment visits.

FIG. 6B describes changes in percentage of CD41 Tregs following treatment with belumosudil compared with baseline for Tregs (regulatory T cells responders). Predose peripheral blood samples were collected on C1D1 (cycle 1 day 1), C2D1 (cycle 2 day 1), C4D1 (cycle 4 day 1), C7D1 (cycle 7 day 1), and end-of-treatment visits.

FIG. 6C describes changes in percentage of CD41 Tregs following treatment with belumosudil compared with baseline for Tregs (regulatory T cells nonresponders). Predose peripheral blood samples were collected on C1D1 (cycle 1 day 1), C2D1 (cycle 2 day 1), C4D1 (cycle 4 day 1), C7D1 (cycle 7 day 1), and end-of-treatment visits.

DETAILED DESCRIPTION

Overview

Figure 1:
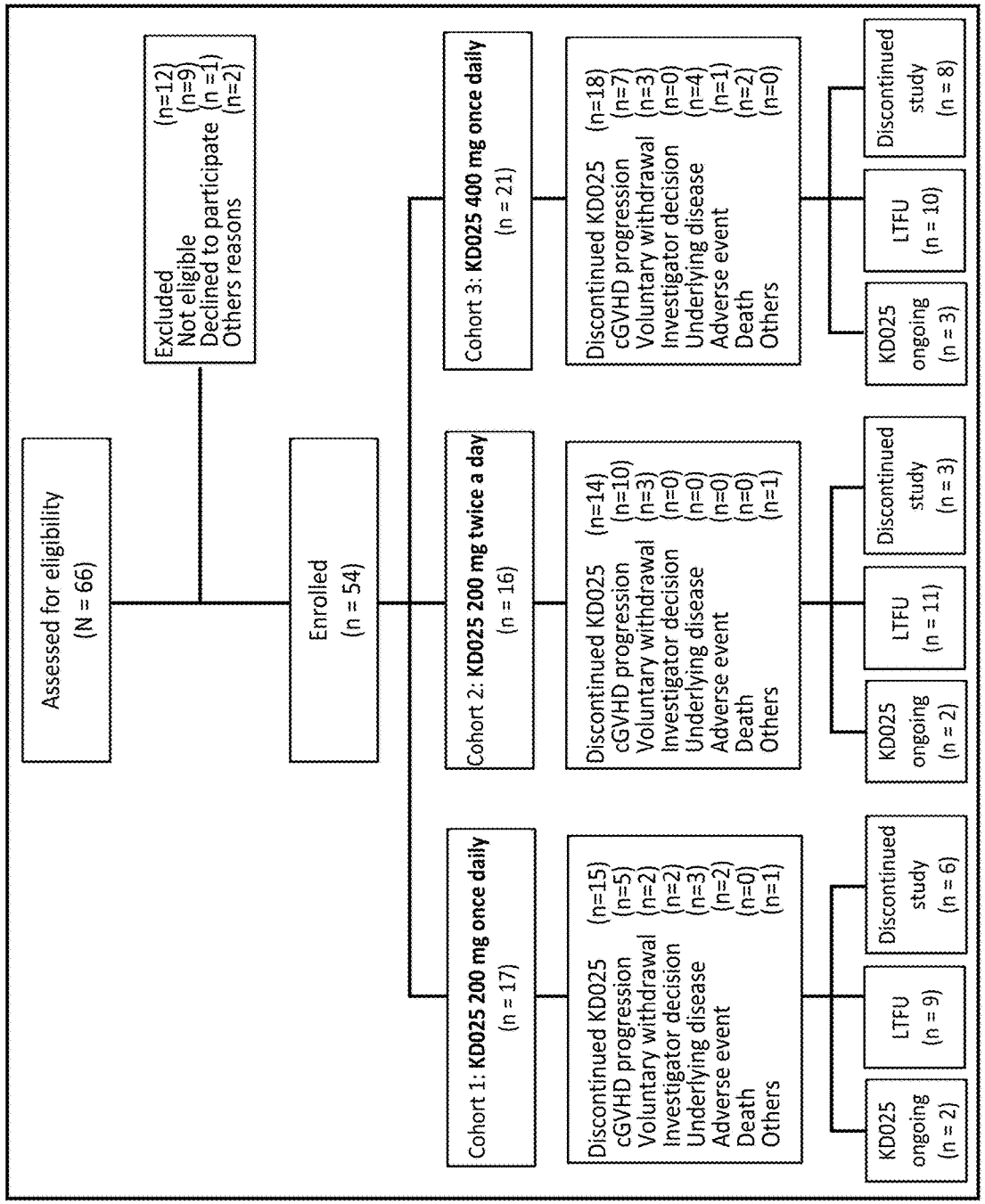
FIG. 1 is the CONSORT flow diagram describing the phase IIa, open-label, dose-finding study of belumosudil of Example 1.

Belumosudil is an oral selective rho-associated coiled-coil-containing protein kinase-2 (ROCK2) inhibitor. ROCK2 inhibition acts on the dysregulated adaptive immune system and the fibrosis that occurs because of aberrant tissue repair. Belumosudil inhibits ROCK2 and ROCK1 with $IC_{50}$ values of approximately 100 nM and 3 µM, respectively.

Belumosudil down-regulated proinflammatory responses via regulation of STAT3/STAT5 phosphorylation and shifting Th17/Treg balance in ex-vivo or in vitro-human T cell assays. Belumosudil also inhibited aberrant pro-fibrotic signaling, in vitro. By controlling ROCK2 activity, belumosudil mediates signaling in immune cellular function and fibrotic pathways, thereby alleviating the effects caused by this debilitating disease, such as inflammation of multiple tissues and fibrotic changes that may involve several organs including the lungs, hepatobiliary system, musculoskeletal system, gastrointestinal (GI) tract, and skin.

In vivo, belumosudil demonstrated activity in animal models of chronic GVHD.

The mesylate salt of belumosudil is marketed as REZUROCK™ in the United States and other countries for the treatment of patients with chronic GVHD (cGVHD), in some instances after failure of at least two prior lines of systemic therapy. The compound belumosudil has the chemical name: 2-{3-[4-(1H-indazol-5-ylamino)-2-quinazolinyl]phenoxy}-N-(propan-2-yl) acetamide. The compound belumosudil is also known as KD025. The active pharmaceutical ingredient of REZUROCK™ is belumosudil mesylate salt with the molecular formula $C_{27}H_{28}N_6O_5S$, a molecular weight of 548.62 g/mol, and having the chemical name 2-{3-[4-(1H-indazol-5-ylamino)-2-quinazolinyl]phenoxy}-N-(propan-2-yl) acetamide methanesulfonate (1:1).

The chemical structure of belumosudil mesylate is as follows:

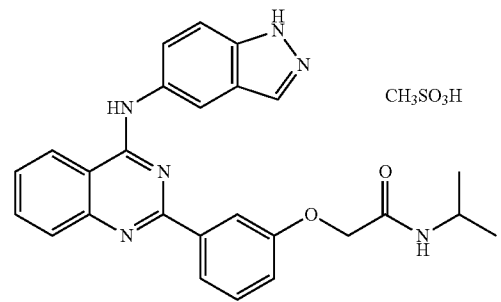

Belumosudil and processes for making the compound are described in the following US patents: U.S. Pat. Nos. 8,357,693, 9,815,820, 10,183,931, and 10,696,660.

The present disclosure provides methods of administering belumosudil mesylate (REZUROCK™) to patients with risk management steps to address potential adverse reactions.

Definitions

"About" as used herein includes the exact amount modified by the term, about, as wells as an amount that would be expected to be within experimental error, such as for example, within 15%, 10%, or 5%. For example, "about 200 mg" means "200 mg" and also a range of mgs that is within experimental error, e.g., plus or minus 15%, 10%, or 5% of 200 mg. As used herein, the term "about" may be used to modify a range and also, a particular value.

"Administering" or "administered to" as used herein (for example, including use of this term with reference to cease administration, and/or resuming administration, of API, including Compound or belumosudil, to a subject), refers to the act of prescribing medicine(s) containing the API for the subject to take during treatment, the act of dispensing the medicine(s) to the subject, and/or the act of physically receiving or ingesting the medicine(s). Thus, the API (e.g., Compound or belumosudil), can be "administered" by a physician or other medical professional who writes prescriptions for medicine(s); and/or by a pharmacist who fills said prescriptions and/or dispenses the medicine(s) to the subject; and/or by the patient or subject who ingests the medicine and/or his or her partner or caretaker who provides the medicine to a subject, each of whom also may "cease" administration and/or "resume" administration of the API.

An "Adverse Reaction" means a physiological response attributable to treatment with an API that is undesired and detrimental or discomforting to the patient or course of treatment. In certain embodiments, adverse reactions include, without limitation, infections, gastrointestinal disorders, respiratory, thoracic, or mediastinal disorders, vascular disorders, musculoskeletal or connective tissue disorders, nervous system disorders, metabolic disorders, and/or skin and subcutaneous disorders.

In other embodiments, more common adverse reactions may include, without limitation, asthenia, nausea, diarrhea, dyspnea, cough, edema, hemorrhage, abdominal pain, musculoskeletal pain, headache, phosphate decreased, gamma glutamyl transferase increased, lymphocytes decreased, and hypertension. Adverse reactions may be detected directly or indirectly.

"API" means "active pharmaceutical ingredient."

"Allogeneic hematopoietic stem cell transplantation (allo-HSCT)" also called bone marrow transplantation or stem cell transplantation, or "allogeneic hematopoietic cell transplantation (allo-HCT)" refers to a procedure where hematopoietic cells from a donor are grafted into a recipient who is not an identical twin. The source of hematopoietic stem cells for allogeneic transplantation may be peripheral blood stem cells (PB SC) or bone marrow (BM). In some circumstances umbilical cord blood may be used. The donor and recipient may be matched at the human leukocyte antigen (HLA) genes, such as siblings. The donor and recipient may be a parent and a child who are only half-matched (haploidentical).

When the term "belumosudil" is used herein, it should be understood that, unless the context clearly indicates otherwise, the term may cover the compound belumosudil in any form as well as pharmaceutically acceptable salts thereof. The term "belumosudil" refers both to the compound belumosudil (for example, in the free base form, amorphous form, or crystalline form), to pharmaceutically acceptable salts of belumosudil, for example, the mesylate salt form as used in as REZUROCK,™ and to any form of belumosudil that may be used in a formulation or pharmaceutical composition for administering the compound to a patient.

"Ceasing" or "cessation" when used regarding administration of an API means that the API is no longer being administered to the patient on either a temporary or permanent basis. For example, if the patient experiences a treatment-related Grade 3 adverse reaction, administration of the API may be "ceased" possibly temporarily (and resumed if the patient recovers to Grade 0 or 1), or if the patient experiences a treatment-related Grade 4 adverse reaction, administration of the API should be permanently ceased or discontinued.

"Clinical endpoint" or "study endpoint" refers to an event or outcome in a clinical trial that can be measured objectively to determine outcomes and potential beneficial effects of the drug or administration protocol as designed in the clinical trial. Examples of clinical endpoints include the following. Overall response rate (ORR) is the percentage of people in a study or treatment group who have a partial response (PR) or complete response (CR) to the treatment within a certain period of time. Failure-free survival (FFS) means the time from the first dose of belumosudil to a failure event, or the interval between the start of belumosudil and the addition of a new cGVHD therapy, relapse of the underlying disease, or nonrelapse mortality (NRM). Overall survival (OS) means the length of time from either the date of diagnosis or the start of treatment for a disease. Duration of response (DOR) means from the time of initial response (e.g., PR or CR) until documented progression from best response of cGVHD, time from initial response to start of additional systemic cGVHD therapy, or death. Time to next treatment (TTNT) means time to initiation of a subsequent systemic cGVHD therapy.

"Clinically recommended amount" or "clinically recommended dose" refers to the amount or dosage of API that has been recommended and/or approved for administration to a patient by those skilled in the field of medicinal chemistry to treat the disease state in question following clinical trials, for example, as described in Examples 1 and 2 hereof. In some embodiments, the clinically recommended dose of belumosudil mesylate is 200 mg a day, in some embodiments, 200 mg a day orally administered with food.

"CYP3A" refers to the CYP3A family of p-450 isoenzymes including CYP3A4.

When the term "Grade" is used to refer to the grade level of an adverse reaction, the term is intended to be defined in accordance with Common Terminology Criteria for Adverse Events (CTCAE), version 5.0 scale. The CTCAE displays Grades 1 through 5 with unique clinical descriptions of severity for each adverse reaction based on the general guidelines: Grade 1—Mild (asymptomatic or mild symptoms; clinical or diagnostic observations only; intervention not indicated); Grade 2—Moderate (minimal, local or non-invasive intervention indicated); Grade 3—Severe (medically significant but not immediately life-threatening; hospitalization or prolongation of hospitalization indicated; disabling; limiting self-care); Grade 4—Life-threatening (urgent intervention indicated); and Grade 5—Death.

"Immunosuppressive therapy" (IST) refers to therapy that is typically administered for at least six months after allo-HSCT to try to prevent GVHD. Examples of IST's include sirolimus, prednisone and calcineurin inhibitors such as tacrolimus and cyclosporine.

Lee Symptom Scale (LSS) summary score measures the effect on patients' functioning and well-being. The Lee Symptom Scale is a 30-item scale developed to measure the symptoms of cGVHD and is described in Lee S J, et al., *Development and validation of a scale to measure symptoms of chronic graft-versus host disease*. Biol Blood Marrow Transplant 2002; 8:444-452.

"Line of treatment" or "line of therapy" describes the sequence or order in which different therapies are given to a patient as the patient's disease progresses. Initial treatment (first-line therapy) may not work or may stop working after a period. After first-line therapy is discontinued, a second different treatment (second-line therapy) may be given. Subsequent lines of therapy may be given when a second-line therapy does not work or stops working. Some patients may be administered multiple lines of therapy over the course of a disease.

First-line therapy for National Institutes of Health (NIH)—defined moderate to severe chronic graft-versus-host disease (cGVHD) may be corticosteroids alone or in combination with sirolimus or a calcineurin inhibitor. (Carpenter P A, et al.: *A phase II/III randomized, multicenter trial of prednisone/sirolimus versus prednisone/sirolimus/calcineurin inhibitor for the treatment of chronic graft-versus-host disease*: BMT CTN 0801. Haematologica 103: 1915-1924, 2018).

Examples of corticosteroid therapies for treatment of cGVHD include, but are not limited to, prednisone, prednisolone, methylprednisolone, and budesonide. Examples of prior systemic therapies for treating cGVHD include, but are not limited to, prednisone, tacrolimus, extracorporeal photopheresis (ECP), sirolimus, ibruitinib, ruxolitinib, mycophenolate mofetil (MMF), rituximab, methotrexate (MTX), cyclosporine, imatinib, ixazomib, and ofatumumab.

"Monitoring" with reference to assessment of adverse reactions means observing, checking, and/or assessing the progression of one or more adverse reaction(s) over at least two points in time; in some embodiments, over a period of time; in some embodiments, monthly; in some embodiments, at least monthly. The monitoring can be performed via consultation, patient self-reporting, visual observation, physical examination, use of devices, laboratory testing, and/or any other means for detecting the adverse reactions, directly or indirectly. Any person who may be involved with administration of the API to a subject, as defined above, may also be involved with monitoring adverse reactions.

"Myeloablative transplant" refers to a transplantation process using very high doses of chemotherapy or radiation prior to transplantation with autologous or allogeneic hematopoietic stem cells. A non-myeloablative transplant, or reduced intensity transplant, involves the patient having less intensive chemotherapy before transplantation with allogeneic hematopoietic stem cells.

"NIH lung symptom score" or "NIH cGVHD lung score" is a clinical symptom-based score ranging from 0 to 3. A Score 0 is used for no symptoms, Score 1 is used for symptoms of shortness of breath with stairs, Score 2 is used for symptoms of shortness of breath on flat ground, and Score 3 is used for shortness of breath at rest or requiring oxygen.

"Or" is used in the inclusive sense (equivalent to "and/or") unless the context requires otherwise.

"Patient" or "subject" as used herein includes an animal or a human, in one embodiment, a human.

"Pharmaceutical composition" means a mixture of substances suitable for administering to an individual that includes a pharmaceutical agent. For example, a pharmaceutical composition may comprise a sterile aqueous solution or the API formulated in an oral dosage form such as a tablet or capsule.

"Pharmaceutically acceptable salt" means a physiologically and pharmaceutically acceptable salt of a compound provided herein. A "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

"Risk" as used herein, for example, with reference to an adverse event, means there is a possibility, even if slight or remote, of the adverse event taking place.

"Side effect" means any physiological response attributable to a treatment with an API other than the disease or disorder for which the API is being administered. A side effect may include an "Adverse Event" (or AE) or "Adverse Reaction" or may be a harmless or even beneficial side effect.

"Steroid-refractory" (SR) cGVHD is defined as cGVHD progression while on steroids or corticosteroids; in one embodiment, while on prednisone.

"Treatment emergent" when used with reference to an adverse reaction or adverse event means that the adverse reaction or event, or symptoms thereof, manifested during a time period when the patient was exposed to the API (e.g., emerged during the course of treatment).

"Treatment-related" when used with reference to an adverse reaction or adverse event means that a treatment-emergent adverse reaction arose or worsened during a period of exposure to the API and based on clinical assessment of a patient's diagnosis, condition(s) and/or physiological profile, was more likely attributable to exposure to the API than other causes or pre-existing conditions (other than the disease-state for which treatment is being provided). For example, if clinical assessment of the patient informs that the adverse reaction(s) were related to pre-existing diseases or disorders and unlikely related to the API, then the adverse reaction will not be considered "treatment related."

A "therapeutically effective amount" of an API means an amount which, when administered to a human for treating a disease (for example, cGVHD), is sufficient to effect treatment for the disease state being treated. As applied to cGVHD in a human, "treating" or "treatment" includes (1) reducing the risk of developing cGVHD and/or inhibiting cGVHD, i.e., arresting or reducing the development of cGVHD or its clinical symptoms; and (2) relieving cGVHD, i.e., causing regression, reversal, or amelioration of the cGVHD or reducing the number, frequency, duration or severity of its clinical symptoms.

The therapeutically effective amount of an API may vary depending upon the health and physical condition of the subject to be treated, the extent of disease progression, the assessment of the medical situation, and other relevant factors. It is expected that the therapeutically effective amount may fall within a range that can be determined through trial and through reference to clinical trial data and results, for example, as described in Examples 1 and 2 hereof and in scientific literature.

Exemplary Embodiments

In one embodiment, the present disclosure provides for use of 2-{3-[4-(1H-indazol-5-ylamino)-2-quinazolinyl]phenoxy}-N-(propan-2-yl) acetamide, or a pharmaceutically acceptable salt thereof (Compound) in a patient who experiences one or more treatment-related, adverse reactions while receiving a clinically-recommended dose of the Compound comprising:
  ceasing administration of the Compound to the patient if the patient experiences at least one adverse reaction at a Grade 3 level or higher; and
  resuming administration of the Compound at a clinically recommended dose for the patient if the at least one adverse reaction did not rise to a Grade 4 level and the patient recovered to a Grade 1 level or less after treatment was ceased.

In one embodiment, the present disclosure provides for use of the Compound, or belumosudil mesylate, comprising the steps of:
  administering the Compound to the patient at a clinically recommended dose for the patient;
  monitoring the patient for adverse reactions;
  ceasing administration of the Compound to the patient if the patient experiences at least one adverse reaction at a Grade 3 level; and
  resuming administration of the Compound to the patient when the patient's at least one adverse reaction has recovered to Grade 1 or less.

In some embodiments, the patient's at least one adverse reaction has recovered to Grade 0 after cessation of Compound administration, and administration is resumed.

In some embodiments, the patient's at least one adverse reaction is Grade 4, wherein administration of the Compound to the patient is permanently discontinued.

In some embodiments, the patient is monitored for adverse reactions over a period of time; in some embodiments, the monitoring occurs monthly; in some embodiments, at least monthly.

In some embodiments, the disclosure provides for use of a clinically recommended dose for the patient that is 200 mg a day prior to and after the patient experiences one or more treatment-related, adverse reactions.

In some embodiments, the disclosure provides for use of a clinically recommended dose for the patient that is 200 mg taken once daily with food, either before and/or after the one or more adverse reactions.

In some embodiments, the disclosure provides for use of a clinically recommended dose for the patient at 400 mg a day prior to and after the patient experiences one or more treatment-related adverse reactions; in some embodiments, this dose is administered to the patient if the patient is also administered one or more PPIs and/or CYP3A inducers, in some embodiments, one or more strong CYP3A4 inducers.

In some embodiments, the disclosure provides for use of a clinically recommended dose for the patient that is reduced after the patient recovers to a Grade 1 level or less and administration of the Compound is resumed, for example, as compared with the clinically recommended dose administered to the patient before the at least one adverse reaction arose.

In some embodiments, the disclosure provides for use of a clinically recommended dose for the patient that is in the range of 200 mg a day to 400 mg a day.

In some embodiments, the patient is being treated for chronic graft-versus-host disease (cGVHD); in some embodiments, the patient is being treated for cGVHD wherein the patient has failed at least two prior lines of systemic therapy for the cGVHD.

In some embodiments, the disclosure provides for use of the Common Terminology Criteria for Adverse Events (CTCAE), for assessing or grading the severity of a patient's adverse reactions; in some embodiments, the CTCAE version is 5.0.

In some embodiments, the patient experiences at least one adverse reaction that is an infection, asthenia, nausea, diarrhea, dyspnea, cough, edema, hemorrhage, abdominal pain, musculoskeletal pain, headache, phosphate decrease, gamma glutamyl transferase increase, lymphocytes decrease, or hypertension.

In some embodiments, the patient experiences at least one adverse reaction that is a viral infection, a bacterial infection, or an infection of unspecified pathogen.

In some embodiments, the patient experiences at least one adverse reaction that is an infection of unspecified pathogen which is acute sinusitis, device related infection, ear infection, folliculitis, gastroenteritis, gastrointestinal infection, hordeolum, infectious colitis, lung infection, skin infection, tooth infection, urinary tract infection, wound infection, upper respiratory tract infection, pneumonia, conjunctivitis, sinusitis, respiratory tract infection, bronchitis, sepsis, or septic shock.

In some embodiments, the patient experiences at least one adverse reaction that is asthenia, edema, or pyrexia.

In some embodiments, the patient experiences at least one adverse reaction that is a gastrointestinal disorder; in some embodiments, the gastrointestinal disorder is nausea, diarrhea, abdominal pain, or dysphagia.

In some embodiments, the patient experiences at least one adverse reaction that is a respiratory, thoracic or mediastinal disorder; in some embodiments, dyspnea, cough, or nasal congestion.

In some embodiments, the patient experiences at least one adverse reaction that is a vascular disorder; in some embodiments, hemorrhage or hypertension.

In some embodiments, the patient experiences at least one adverse reaction that is a musculoskeletal or connective tissue disorder; in some embodiments, the musculoskeletal or connective tissue disorder is musculoskeletal pain, muscle spasm, or arthralgia.

In some embodiments, the patient experiences at least one adverse reaction that is a nervous system disorder; in some embodiments, headache or migraine headache.

In some embodiments, the patient experiences at least one adverse reaction that is a metabolic disorder; in some embodiments, the metabolic disorder is decreased appetite.

In some embodiments, the patient experiences a skin or subcutaneous disorder; in some embodiments, the skin or subcutaneous disorder is a rash or pruritus.

In other embodiments, the present disclosure provides a method of treating a patient who experiences one or more treatment-related, adverse reactions while receiving a clinically-recommended dose of 2-{3-[4-(1H-indazol-5-ylamino)-2-quinazolinyl]phenoxy}-N-(propan-2-yl) acetamide, or a pharmaceutically acceptable salt thereof (Compound), comprising:
  ceasing administration of the Compound to the patient if the patient experiences at least one adverse reaction at a Grade 3 level or higher; and
  resuming administration of the Compound at a clinically recommended dose for the patient if the at least one adverse reaction did not rise to a Grade 4 level and the patient recovered to a Grade 1 level or less after treatment was ceased.

In some embodiments, the method provided by the disclosure comprises the patient experiencing at least one adverse reaction at a Grade 3 level and resuming administration of the Compound to the patient when the patient's at least one adverse reaction has recovered to Grade 1 or less.

In some embodiments, the method provided by the disclosure comprises the patient experiencing at least one adverse reaction at a Grade 4 level and permanently ceasing administration of the Compound to the patient.

In embodiments disclosure herein, including in the uses and methods of treatment provided herein, the clinically recommended dose for the patient may be in the range of 200 mg a day to 400 mg a day; in some embodiments, the clinically recommended dose for the patient is 200 mg a day; in some embodiments, the clinically recommended dose for the patient is a reduced dose after the patient recovers to a Grade 1 level or less and administration of the Compound is resumed, as compared with the clinically recommended dose administered before the patient experienced at least one adverse reaction.

In some embodiments, the subject has had allogeneic hematopoietic stem cell transplantation that is a matched-HSCT. In some embodiments, the allogeneic hematopoietic stem cell transplantation is a haploidentical-HSCT.

In some embodiments, belumosudil treatment is continued based on the patient's tolerability until active cGVHD symptoms resolve or progress. The number of cycles and duration of the treatment is patient dependent. In some embodiments, the belumosudil is administered to the patient in one or more 28-day cycles.

In some embodiments, the number of cycles ranges from 3 to 15. In some embodiments, the number of cycles ranges from 3 to 14, from 3 to 13, from 3 to 12, from 3 to 11, from 3 to 10, from 3 to 9, from 3 to 8, from 3 to 7, from 3 to 6, from 3 to 5, or from 3 to 4. In some embodiments, the number of cycles ranges from 5 to 11. In some embodiments, the number of cycles ranges from 6 to 12. In some embodiments, the number of cycles ranges from 5 to 10, from 5 to 9, or from 5 to 8. In some embodiments, the number of cycles ranges from 5 to 7. In some embodiments, the number of cycles ranges from 5 to 6. In some embodiments, the number of cycles is 5. In some embodiments, the number of cycles is 6. In some embodiments, the number of cycles is 7. In some embodiments, the number of cycles is 3, 4, 6, 7, 8, 9, 10, 11, 12, 13, 14, or 15.

In some embodiments, the number of cycles ranges from 3 cycles to loss of response. In some embodiments, the number of cycles ranges from 4 cycles to loss of response. In some embodiments, the number of cycles ranges from 5 cycles to loss of response. In some embodiments, the number of cycles ranges from 6 cycles to loss of response. In some embodiments, the number of cycles ranges from 7 cycles to loss of response. In some embodiments, the number of cycles ranges from 8 cycles to loss of response. In some embodiments, the number of cycles is greater than 3, 4, 5, 10, 15, 20, 25, or 30, or until a desired response is achieved.

In some embodiments, the subject experiences an improvement as defined by the Lee Symptom Scale (LSS). In some embodiments, the subject experiences at least a 7-point reduction in the LSS score. In some embodiments, the subject experiences at least a 10-point reduction in the LSS score. In some embodiments, the improvement is maintained over at least two consecutive evaluations. In some embodiments the LSS score is evaluated at baseline and on day 1 of each cycle starting at cycle 2 day 1.

In some embodiments, the subject has chronic graft-versus-host disease and has failed one to three prior lines of systemic therapy for the chronic graft-versus-host disease. In some embodiments, the subject has chronic graft-versus-host disease and has failed at least two prior lines of systemic therapy for the chronic graft-versus-host disease. In some embodiments, the subject has chronic graft-versus-host disease and has failed two to five prior lines of systemic therapy for the chronic graft-versus-host disease. In some embodiments, the subject has failed at least one, at least two, at least three, at least four, at least five, at least six, at least seven, at least eight, at least nine or at least ten prior lines of systemic therapy for the chronic graft-versus-host disease.

In some embodiments, the subject experienced a complete response to last treatment for the graft-versus-host disease prior to belumosudil. In some embodiments, the subject experienced a partial response to last treatment for the graft-versus-host disease prior to belumosudil. In some embodiments, stable disease during the last treatment for the graft-versus-host disease prior to belumosudil.

In some embodiments, the prior lines of systemic therapy for the chronic graft-versus-host disease have been discontinued.

In some embodiments, the prior lines of systemic therapy are selected from the group consisting of prednisone, tacrolimus, ECP, sirolimus, ibruitinib, ruxolitinib, MMF, rituximab, MTX, cyclosporine, imatinib, ixazomib, and ofatumumab.

In some embodiments, the cGVHD is steroid-refractory (SR) cGVHD. In some embodiments, the subject is refractory to the last line of treatment prior to belumosudil treatment.

In some embodiments, the subject is receiving concomitant corticosteroid therapy. In some embodiments, the concomitant corticosteroid therapy is selected from the group consisting of prednisone, prednisolone, methylprednisolone, and budesonide. In some embodiments, the concomitant corticosteroid therapy is prednisone. In some embodiments, the dose of the concomitant corticosteroid therapy is reduced after at least 1 cycle of the belumosudil treatment. In some embodiments, the dose of the concomitant corticosteroid therapy is reduced by at least about 10%, by at least about 20%, by at least about 30%, by at least about 40%, by at least about 50%, by at least about 60%, or by at least about 70% after at least 1 cycle of the belumosudil treatment. In some embodiments, the dose of the concomitant corticosteroid therapy is reduced by from about 10% to about 70%, from about 15% to about 65%, from about 20% to about 60%, from about 30% to about 60%, from about 35% to about 60%, from about 40% to about 60%, or from about 45% to about 55% after at least 1 cycle of the belumosudil treatment. In some embodiments, the concomitant corticosteroid therapy is discontinued after at least 1 cycle of the belumosudil treatment.

In some embodiments, the subject is receiving concomitant calcineurin inhibitor therapy.

In some embodiments, the subject has involvement of at least 4 organs. In some embodiments, the subject has involvement of at least 3 organs. In some embodiments, the subject has involvement of at least 2 organs.

Belumosudil Tablets

In one embodiment, the belumosudil is formulated into a tablet for oral administration. Belumosudil mesylate is a yellow powder that is practically insoluble in water. Belumosudil tablets may be prepared for oral administration. Each tablet contains 200 mg of the free base equivalent to 242.5 mg of belumosudil mesylate. The tablet also may contain the following inactive ingredients: microcrystalline cellulose, hypromellose, croscarmellose sodium, colloidal silicon dioxide, and magnesium stearate. The tablet film consists of polyvinyl alcohol, polyethylene glycol, talc, titanium dioxide and yellow iron oxide. Each 200 mg tablet is a pale-yellow film-coated oblong tablet debossed with "KDM" on one side and "200" on the other side. Tablets are stored at room temperature, 20° C. to 25° C. (68° F. to 77° F.); excursions permitted from 15° C. and 30° C. (59° F. to 86° F.).

Overview

The following abbreviations may be helpful in considering the Examples and description herein.

Abbreviations

| | |
|---|---|
| AE | Adverse events |
| AR | Adverse reaction |
| AMS | Accelerator mass spectrometry |
| alloHCT | allogeneic hematopoietic cell transplantation |
| BID | Twice daily (bi-daily) |
| BM | Bone marrow |
| cGVHD | Chronic graft versus host disease |
| CMV | cytomegalovirus |
| CR | Complete response |
| CTCAE | Common Terminology Criteria for Adverse Events |
| DDI | Drug-drug interaction |
| DOR | Duration of response |
| EOI | End of infusion |
| FFS | Failure-free survival |
| HLA | human leukocyte antigen |
| IST | Immunosuppressive therapy |
| IV | Intravenous |
| LSC | Liquid scintillation counting |
| LSS | Lee Symptom Scale |
| NMT | Not more than |
| ORR | Overall response rate |
| OS | Overall survival |
| PBSC | peripheral blood stem cells |
| PPI | Proton pump inhibitors |
| PR | Partial response |
| QOL | Quality of life |
| SD | Standard deviation |
| SR | Steroid refractory |
| TEAEs | treatment-emergent adverse events |
| TTNT | Time to next treatment |
| QD | Daily; every day |

EXAMPLES

Example 1: A Phase IIa, Open-Label, Dose-Finding Study of Belumosudil

Subject Eligibility

Eligible patients were allogeneic bone marrow transplant or allogeneic hematopoietic cell transplant (alloHCT) recipients of age≥18 years with persistent cGVHD manifestations after having received one to three prior systemic lines of therapy and who were receiving corticosteroid treatment with or without a calcineurin inhibitor and/or concurrent extracorporeal photopheresis. Belumosudil was continued until cGVHD progression or unacceptable toxicity.

Study Design and Treatment

Patients were enrolled into three sequential cohorts: cohort one received belumosudil 200 mg once daily, cohort two received belumosudil 200 mg twice daily (twice a day), and cohort three received belumosudil 400 mg once daily. (FIG. 1) Before enrollment of the subsequent cohort, safety data in each previous cohort were analyzed after eight patients reached two months of treatment to assure that there was no safety signal. The 2-month timeframe was selected because all clinically significant belumosudil-related adverse events (AEs) to date had occurred in ≤36 days of starting belumosudil. No safety concerns were identified, allowing for planned dose escalation.

Belumosudil was administered orally in 28-day cycles until disease progression or unacceptable toxicity. Progression was defined per the 2014 NIH cGVHD Consensus Criteria. Long-term follow-up was conducted every 8 weeks until study closeout. After 4 weeks of belumosudil therapy, corticosteroid therapy could be tapered at the investigators' discretion. Screening was conducted within 28 days of the first study dose. Response was initially assessed after two cycles; however, this was amended to evaluate response on day 1 of each cycle, starting at cycle 2 day 1.

Study End Points

The primary efficacy end point was ORR, defined as the proportion of patients who achieved either a complete response (CR) or partial response (PR), per the 2014 NIH cGVHD Consensus Criteria, at any time point. Only response assessments before the next lines of therapy after belumosudil were counted toward ORR. All responses were assessed by the investigators. Secondary end points included the number and the percentage of patients with steroid-dependent cGVHD who had a best response of PR or CR, duration of response (DOR), response rate by organ system, LSS score, corticosteroid dose reductions, time to next treatment (TTNT), failure-free survival (FFS), and overall survival (OS). The safety and tolerability of belumosudil were evaluated via AE assessments, physical examinations, vital sign measurements, laboratory tests, and electrocardiograms throughout the study. Predose samples were collected for pharmacodynamic (PD) evaluation, which included the assessment of immune cell subtypes in peripheral blood.

Statistical Analysis

With a sample size of 16 patients per cohort, the study had a >90% probability of ≥1 study participants experiencing an AE with an underlying rate of ≥14%, which was derived from the probability calculations of the assumed sample size. Assuming a best ORR of 25%, which was determined to be clinically meaningful, the study was expected to have approximately 90% probability to show a response in ≥2 patients per cohort. This study was not powered to show significant differences between cohorts with respect to efficacy, AEs, or PD analyses. The primary analysis was conducted using the safety population, defined as enrolled patients who received ≥1 dose of study medication. The Clopper-Pearson (exact) method was used to construct the two-sided 95% CI for ORR. The Kaplan-Meier (K-M) method was used to calculate estimates of FFS and OS.

Results

Subjects

A total of Fifty-four patients were enrolled in sequential cohorts: 17 patients in cohort 1, 16 patients in cohort 2, and 21 patients in cohort 3 (FIG. 1). As of the data cutoff for this analysis, the median duration of follow-up was 36 months in cohort 1, 32 months in cohort 2, and 24 months in cohort 3. The overall median duration of follow-up was 29 months (range, 1-39 months).

Demographics and baseline characteristics were overall comparable across cohorts (Table 1, Table 2). The median age at baseline was 52 years (range, 20-75 years). The median time from cGVHD diagnosis to treatment was longest in cohort 1 at 26 months (compared with 18 months and 16 months in cohorts 2 and 3, respectively). Seventy-eight percent of patients had severe cGVHD per investigator assessment. Half of the patients had involvement of ≥4 organs, and more patients in cohort 3 had lung involvement (48%) compared with those in cohorts 1 (24%) and 2 (19%). The baseline median corticosteroid dose (mg/kg/d prednisone equivalent) was 0.22, 0.19, and 0.17 across cohorts, respectively. Patients in cohort 1 had received a median of three prior lines of treatment, whereas patients in cohorts 2 and 3 had received a median of two prior lines of treatment. Seventy-three percent (35 of 48, data not available for six patients) of patients were refractory to their last line of treatment before study enrollment. The CONSORT diagram (FIG. 1) shows patient disposition. The median duration of treatment was 8.5 months (range, 2-39 months) in cohort 1, 7.5 months (range, 1-months) in cohort 2, and 9 months (range, 1-29 months) in cohort 3. Twenty-eight percent of patients have received >18 months of belumosudil. Reasons for discontinuing belumosudil included cGVHD progression (n=22), voluntary withdrawal by patients (n=8), relapse of underlying disease (n=7), investigator decision (n=3), AEs considered to be possibly treatment related (n=3), and death (n=2). LTFU means long-term follow up.

TABLE 1

Baseline Demographics and Clinical Characteristics

| Characteristic | Cohort 1 KD025 200 mg Once Daily (n = 17) | Cohort 2 KD025 200 mg Twice a Day (n = 16) | Cohort 3 KD025 400 mg Once Daily (n = 21) | Total (N = 54) |
|---|---|---|---|---|
| Median age, years (range) | 50 (20-63) | 55 (30-75) | 46 (25-75) | 52 (20-75) |
| Male, n (%) | 13 (77) | 9 (56) | 12 (57) | 34 (63) |
| Indication for transplant, n (%) | | | | |
| AML | 3 (18) | 8 (50) | 9 (43) | 20 (37) |
| ALL | 3 (18) | 2 (13) | 3 (14) | 8 (15) |
| MDS | 2 (12) | 2 (13) | 2 (10) | 6 (11) |
| Non-Hodgkin lymphoma | 3 (18) | 0 | 2 (10) | 5 (9) |
| Other non-Hodgkin lymphoma | 0 | 2 (13) | 1 (5) | 3 (6) |
| Others | 6 (35) | 2 (13) | 4 (19) | 12 (22) |
| Conditioning intensity, n (%)[a] | | | | |
| Myeloablative | 9 (53) | 5 (31) | 10 (48) | 24 (44) |
| Nonmyeloablative | 7 (41) | 8 (50) | 10 (48) | 25 (46) |
| Unknown | 1 (6) | 3 (19) | 1 (5) | 5 (9) |
| Stem-cell source, n (%)[a] | | | | |
| Peripheral blood | 15 (88) | 15 (94) | 18 (86) | 48 (89) |
| Bone marrow | 0 | 0 | 1 (5) | 1 (2) |
| Cord blood | 1 (6) | 0 | 0 | 1 (2) |
| Unknown | 1 (6) | 1 (6) | 2 (10) | 4 (7) |
| HLA matching of donor or recipient, n (%)[a] | | | | |
| Matched | 14 (82) | 13 (81) | 18 (86) | 45 (83) |
| Partially matched | 3 (18) | 3 (19) | 2 (10) | 8 (15) |
| Unknown | 0 | 0 | 1 (5) | 1 (2) |
| CMV-positive serostatus (donor/recipient), n (%) | | | | |
| +/+ | 4 (24) | 4 (25) | 6 (29) | 14 (26) |
| +/− | 1 (6) | 3 (19) | 0 | 4 (7) |
| −/+ | 6 (35) | 4 (25) | 6 (29) | 16 (30) |
| −/− | 3 (18) | 4 (25) | 6 (29) | 13 (24) |
| At least 1 unknown | 3 (18) | 1 (6) | 3 (14) | 7 (13) |
| Median time from cGVHD diagnosis to enrollment, months (range) | 26.4 (0.0-130.7) | 18.0 (1.0-69.9) | 16.0 (1.0-161.9) | 20.0 (0.0-161.9) |
| cGVHD severity, n (%)[b] | | | | |
| Severe | 12 (71) | 14 (88) | 16 (76) | 42 (78) |
| Moderate | 5 (29) | 2 (13) | 4 (19) | 11 (20) |
| Mild | 0 | 0 | 1 (5) | 1 (2) |
| Organ involvement | | | | |
| Median No. of organs involved, n (range) | 3 (2-6) | 4 (1-7) | 3 (2-7) | 3 (2-7) |
| ≥4 organs involved, n (%) | 8 (47) | 10 (63) | 9 (43) | 27 (50) |
| Eyes, n (%) | 14 (82) | 11 (69) | 17 (81) | 42 (78) |
| Skin, n (%) | 13 (77) | 12 (75) | 15 (71) | 40 (74) |
| Mouth, n (%) | 13 (77) | 11 (69) | 11 (69) | 35 (65) |
| Joints and/or fascia, n (%) | 11 (65) | 11 (69) | 12 (57) | 34 (63) |
| Lungs, n (%) | 4 (24) | 3 (19) | 10 (48) | 17 (32) |
| Upper GI, n (%) | 2 (12) | 4 (25) | 2 (10) | 8 (15) |
| Esophagus, n (%) | 2 (12) | 0 | 4 (19) | 6 (11) |
| Lower GI, n (%) | 1 (6) | 2 (13) | 1 (5) | 4 (7) |
| Liver, n (%) | 0 | 2 (13) | 0 | 2 (4) |

TABLE 1-continued

Baseline Demographics and Clinical Characteristics

| Characteristic | Cohort 1 KD025 200 mg Once Daily (n = 17) | Cohort 2 KD025 200 mg Twice a Day (n = 16) | Cohort 3 KD025 400 mg Once Daily (n = 21) | Total (N = 54) |
|---|---|---|---|---|
| Median Karnofsky performance status, n (%) | | | | |
| ≤50 | 0 | 0 | 1 (5) | 1 (2) |
| 60-70 | 4 (24) | 4 (25) | 6 (29) | 14 (26) |
| 80-90 | 13 (77) | 12 (75) | 14 (67) | 39 (72) |
| 100 | 0 | 0 | 0 | 0 |
| Prior therapy characteristics | | | | |
| Median prior LOTs, n | 3 | 2 | 2 | 3 |
| ≥2 prior LOTs, n (%) | 15 (88) | 9 (56) | 14 (67) | 38 (70) |
| Refractory to prior LOT, n (%)[a] | 11/15 (73) | 9/13 (69) | 15/20 (75) | 35/48 (73) |

Abbreviations: ALL, acute lymphocytic leukemia; AML, acute myelogenous leukemia; cGVHD, chronic graft-versus-host disease; CMV, cytomegalovirus; LOT, line of therapy; MDS, myelodysplastic syndrome.

[a]Denominator excludes patients with unknown status (six patients in total).

[b]Disease severity was determined using the Physician-reported Global cGVHD Activity Assessment Form.

TABLE 2

Additional Baseline Demographics

| Characteristic | Cohort 1 KD025 200 mg Once Daily (n = 17) | Cohort 2 KD025 200 mg Twice a Day (n = 16) | Cohort 3 KD025 400 mg Once Daily (n = 21) | Total (N = 54) |
|---|---|---|---|---|
| Prior systemic cGVHD therapy type, No. (%) | | | | |
| CS | 17 (100) | 16 (100) | 21 (100) | 54 (100) |
| Tacrolimus | 8 (47) | 7 (44) | 11 (52) | 26 (48) |
| Sirolimus | 10 (59) | 8 (50) | 6 (29) | 24 (44) |
| Rituximab | 8 (47) | 3 (19) | 5 (24) | 16 (30) |
| ECP | 5 (29) | 4 (25) | 6 (29) | 15 (28) |
| MMF | 4 (24) | 4 (25) | 4 (19) | 12 (22) |
| Cyclosporine | 3 (18) | 0 | 2 (10) | 5 (9) |
| Ibrutinib | 1 (6) | 0 | 3 (14) | 4 (7) |
| MTX | 1 (6) | 2 (13) | 0 | 3 (6) |
| Ixazomib | 1 (6) | 1 (6) | 0 | 2 (4) |
| ATG | 1 (6) | 0 | 0 | 1 (2) |
| Ofatumumab | 0 | 0 | 1 (5) | 1 (2) |
| Imatinib | 1 (6) | 0 | 0 | 1 (2) |
| Ruxolitinib | 0 | 0 | 1 (5) | 1 (2) |
| Continuing systemic cGVHD therapy type | | | | |
| CS, No. (%) | 17 (100) | 16 (100) | 21 (100) | 54 (100) |
| Mean prednisone equivalent dose at enrollment, mg/kg/d | 0.22 | 0.24 | 0.28 | 0.25 |
| CNI, No. (%) | 7 (41) | 6 (38) | 12 (57) | 25 (46) |
| ECP, No. (%) | 4 (24) | 4 (25) | 4 (19) | 12 (22) |

Abbreviations: ATG, antithymocyte globulin; cGVHD, chronic graft-versus-host disease; CNI, calcineurin inhibitor; CS, corticosteroid; ECP, extracorporeal photopheresis; MMF, mycophenolate mofetil; MTX, methotrexate.

Efficacy

Overall response rate. In the safety population (N=54), the ORR (95% CI) was 65% (51% to 77%). The ORR (95% CI) was similar across cohorts: 65% (38% to 86%) in cohort 1, 69% (41% to 89%) in cohort 2, and 62% (38% to 82%) in cohort 3 (Table 3). Efficacy data for subgroups and secondary end points are presented as pooled data across cohorts.

TABLE 3

Efficacy and CS Reduction

| Characteristic | Cohort 1 KD025 200 mg Once Daily (n = 17) | Cohort 2 KD025 200 mg Twice a Day (n = 16) | Cohort 3 KD025 400 mg Once Daily (n =21) | Total (N = 54) |
|---|---|---|---|---|
| ORR, % (95% CI) | 65 (38 to 86) | 69 (41 to 89) | 62 (38 to 82) | 65 (51 to 77) |
| Subgroup analyses, n/N (%, 95% CI) | | | | |
| ≤2 prior LOTs | 10/15 (67, 38 to 88) | 5/8 (63, 25 to 92) | 8/12 (67, 35 to 90) | 23/35 (66, 48 to 81) |
| Refractory to previous LOT | 7/11 (64, 31 to 89) | 6/9 (67, 30 to 93) | 9/15 (60, 32 to 94) | 22/35 (63, 45 to 79) |
| ≤4 organs involved | 4/8 (50, 16 to 84) | 8/10 (80, 44 to 98) | 7/9 (78, 40 to 97) | 19/27 (70, 50 to 86) |
| Severe cGVHD[a] | 8/12 (67, 35 to 90) | 9/14 (64, 35 to 87) | 8/16 (50, 25 to 75) | 25/42 (60, 43 to 74) |
| Clinically significant improvement (LSS)[b] | | | | |
| Overall, n (%, 95% CI) | 9 (53, 28 to 77) | 7 (44, 20 to 70) | 11 (52, 30 to 74) | 27 (50, 36 to 64) |
| Responder, n/N (%, 95% CI) | 8/11 (73, 39 to 94) | 3/11 (27, 6 to 61) | 9/13 (69, 39 to 91) | 20/35 (57, 39 to 74) |
| Nonresponder, n/N (%, 95% CI) | 1/6 (17, 0.4 to 64) | 4/5 (80, 28 to 99) | 2/8 (25, 3 to 65) | 7/19 (37, 16 to 62) |
| Proportion with CS reduction, n (%, 95% CI) | 13 (76, 50 to 93) | 9 (56, 30 to 80) | 14 (67, 43 to 85) | 36 (67, 53 to 79) |
| Mean percent change in CS dose from baseline, % | | | | |
| Overall | −50 | −36 | −47 | −45 |
| Responder | −63 | −36 | −63 | −55 |
| Nonresponder | −26 | −37 | −19 | −26 |
| CS discontinuation, n (%, 95% CI) | 4 (24, 7 to 50) | 2 (13, 2 to 38) | 4 (19, 5 to 42) | 10 (19, 9 to 31) |

Abbreviations: cGVHD, chronic graft-versus-host disease; CS, corticosteroid; LOT, line of therapy; LSS, Lee Symptom Scale; ORR, overall response rate.
[a]Disease severity was determined using the Physician-reported Global cGVHD Activity Assessment Form.
[b]Changes in cGVHD symptom burden were measured by the LSS. Clinically meaningful improvement in symptom burden was defined as a decrease of at least seven points in LSS summary score.

Figure 2:
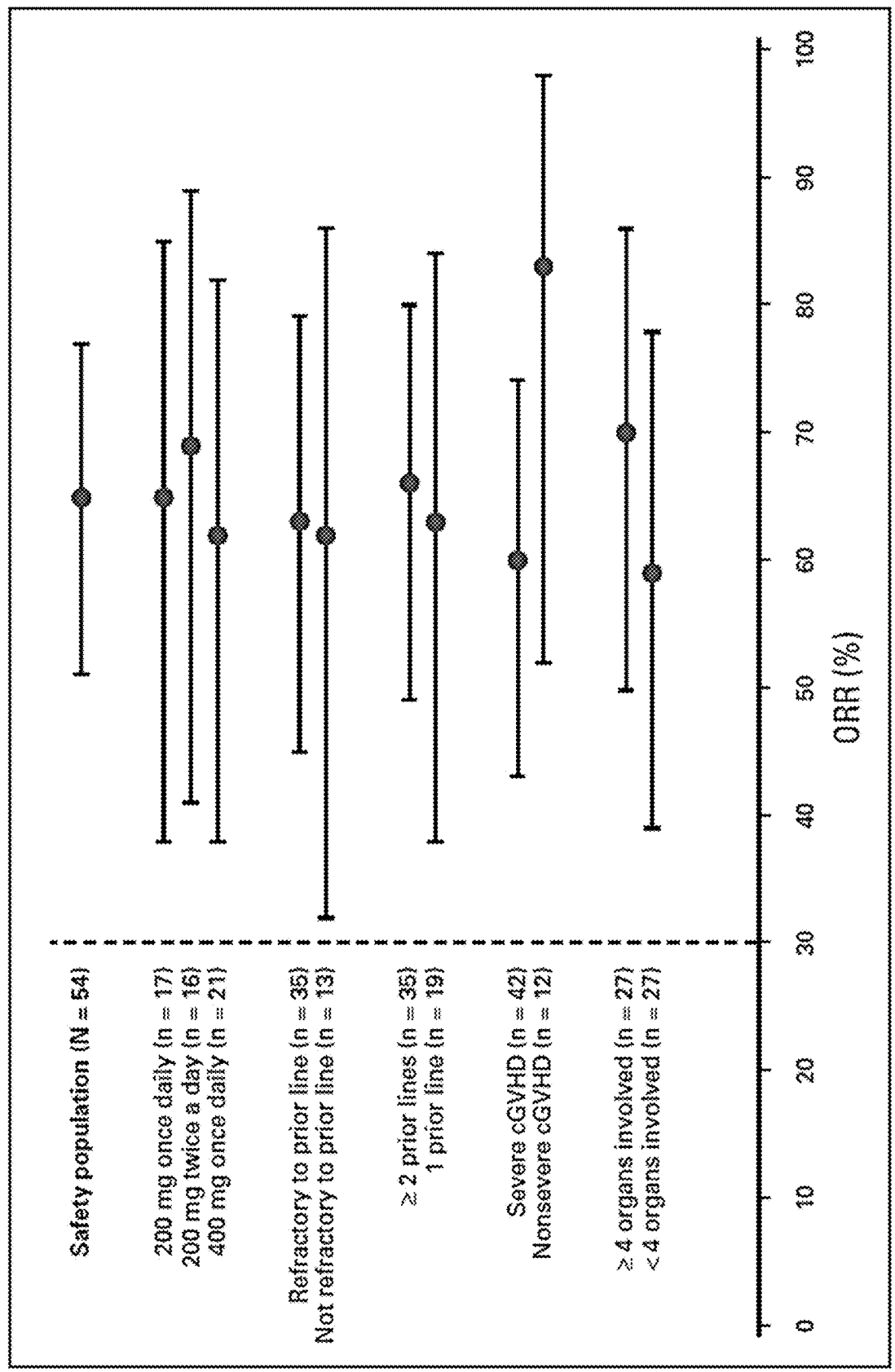
FIG. 2 is a forest plot for subgroup analyses of ORR in the safety population. Subgroups were defined based on baseline assessment.
Figure 3A:
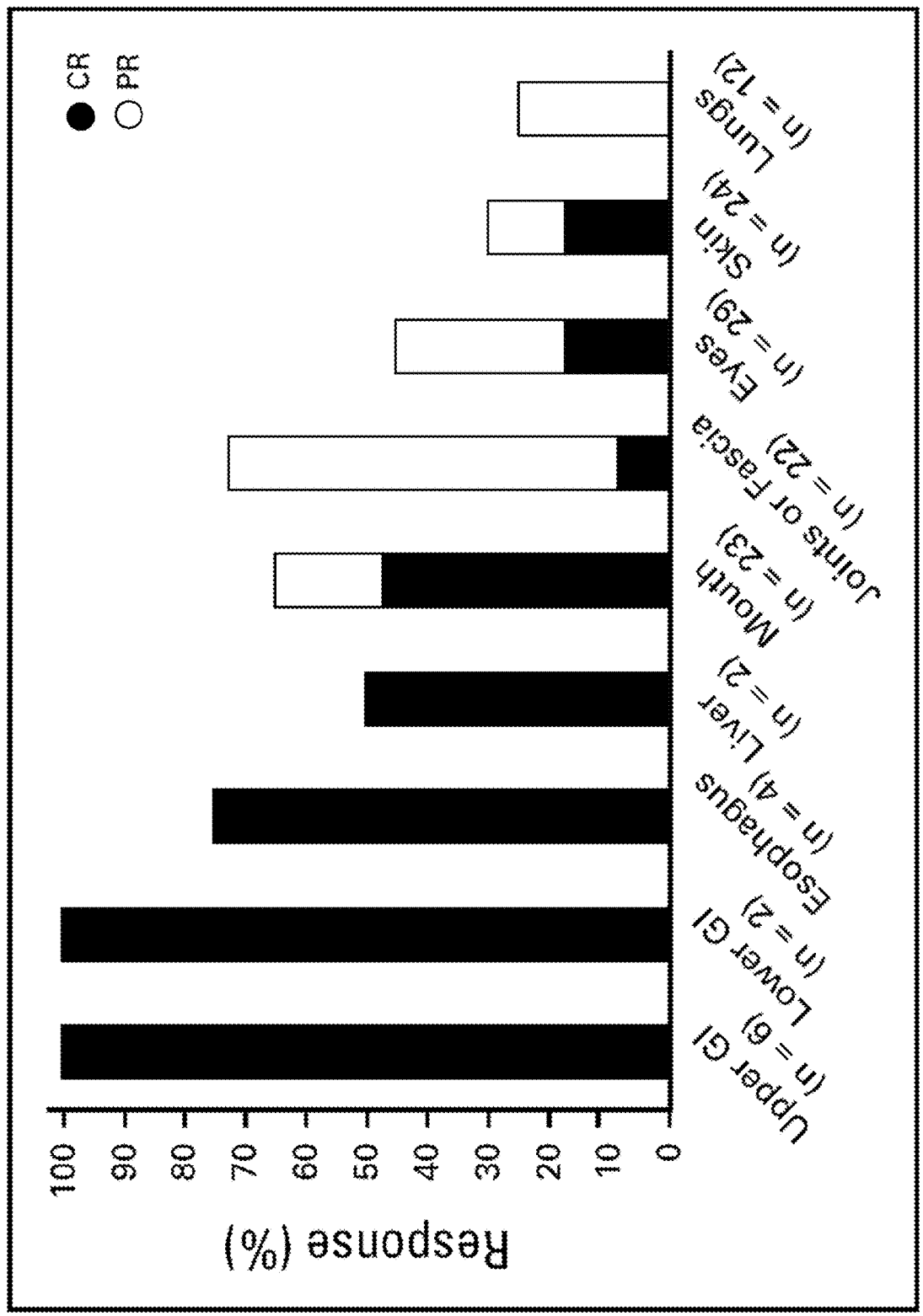
FIG. 3A describes the best individual response by organ system among responders. n=number of responder population for global severity rating and number of specific organs involved at baseline. The percentages are calculated based on the corresponding n.

Responses were achieved across key subgroups, with ORRs of 60% (25 of 42) in patients with severe cGVHD, 66% (23 of 35) in patients who had received ≥2 prior systemic lines of therapy, 63% (22 of 35) in patients who were refractory to their last lines of therapy before enrollment, and 70% (19 of 27) in patients with ≥4 organs involved (FIG. 2). All responses at the patient level were PR; however, organ specific analyses showed that CR was achieved across all affected organs, with the exception of the lungs, where PR was the best response achieved (FIG. 3A and FIG. 3B). FIG. 3B shows for the best response by organ that three partial responses were achieved in lung at the 400 mg once daily dose.

Figure 4A:
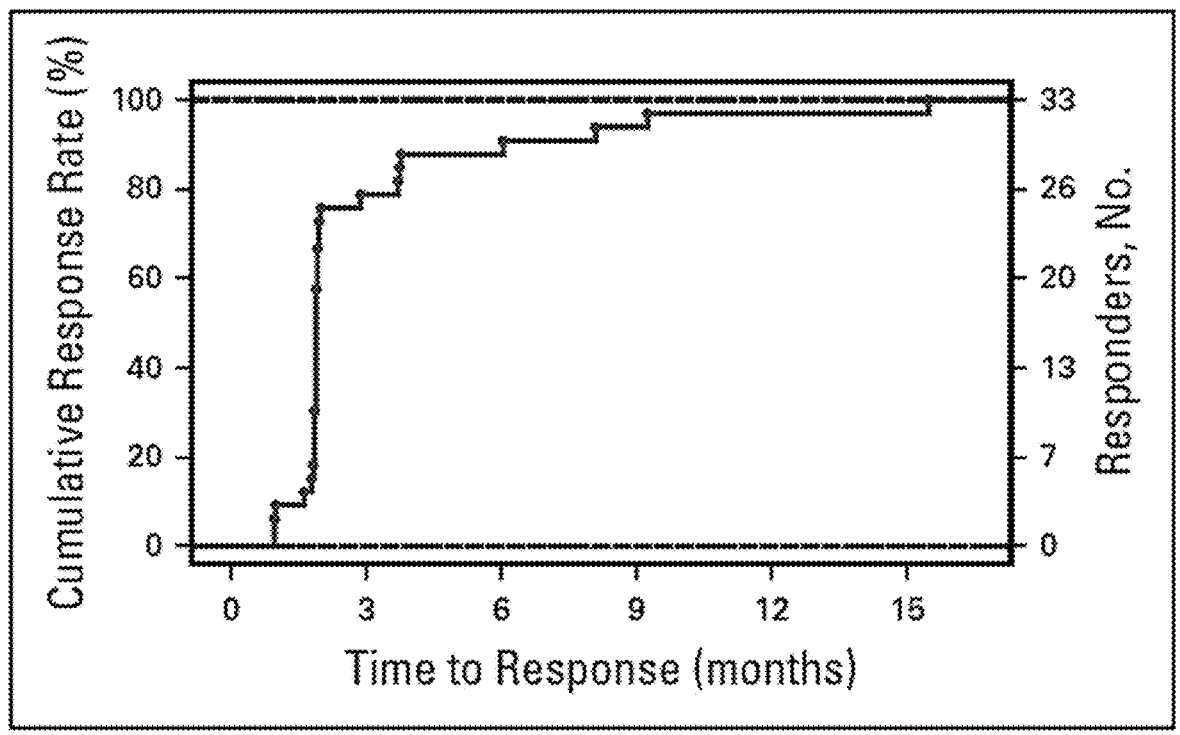
FIG. 4A describes time to response among belumosudil responders. Percentages are calculated based on the number of responder population.
Figure 4B:
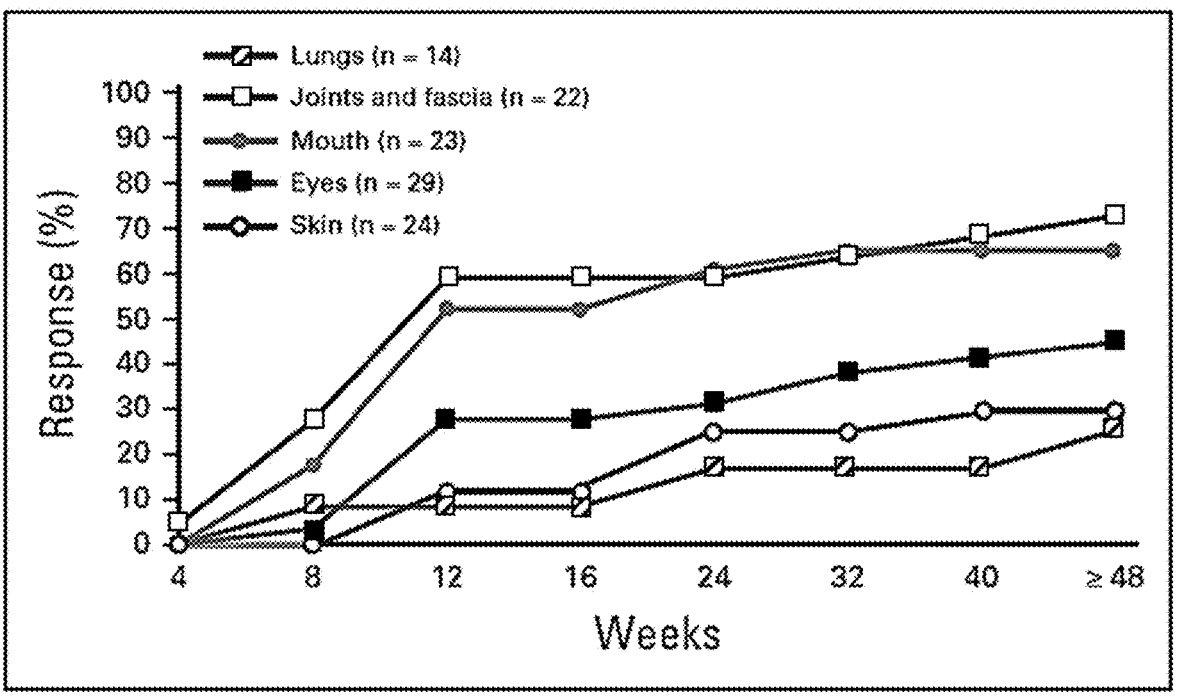
FIG. 4B describes time to response by selected organs among responders. Percentages are calculated based on the number of responder population.

Responses were generally rapid, with >75% of all responses achieved by the first response assessment at week 8 (FIG. 4A). Four of 35 responses occurred after 24 weeks of belumosudil treatment, with late organ responses observed in the lungs, joints and/or fascia, and eyes (FIG. 4B).

Among responders, the K-M median DOR across cohorts was 35 weeks (FIG. 5A). The K-M median DOR was 38 weeks for patients who had received >2 prior systemic lines of therapy.

Time to next treatment. The K-M median TTNT was 14 months (FIG. 5B). Subsequent systemic cGVHD therapies included tacrolimus, sirolimus, ibrutinib, ruxolitinib, extracorporeal photopheresis, and mycophenolate mofetil.

FFS and OS. The FFS rate (95% CI) was 76% (62% to 85%), 47% (33% to 60%), and 33% (21% to 46%) at 6, 12, and 24 months, respectively (FIG. 5C). FFS was defined as the time from the first dose of belumosudil to a failure event. Reasons for failure included initiation of a new systemic therapy (n=27), relapse of the underlying disease (n=7), and death (n=2). An important end point is the percentage of patients achieving FFS with response (CR/PR) at 12 months, which was 24% in this study. The OS rate (95% CI) was 91% (79% to 96%) and 82% (69% to 90%) at 12 and 24 months, respectively (FIG. 5D).

QOL assessment. Clinically meaningful improvement in LSS score, defined as a decrease of ≥7 points in the LSS summary score, during belumosudil treatment was observed in 50% of patients. Thirty-five percent of all patients (37% of responders and 32% of nonresponders) reported a clinically meaningful improvement in LSS score on consecutive assessments.

Corticosteroid sparing. During belumosudil treatment, 67% of patients reduced corticosteroid dose and 19% completely discontinued corticosteroid therapy. The mean corticosteroid dose was reduced by 45%. The median time to corticosteroid therapy discontinuation was 29 weeks (range, 8-77 weeks). The mean corticosteroid dose reduction was 55% in responders and 26% in nonresponders (Table 3).

Safety

Belumosudil was well-tolerated, with >56 patient-years of belumosudil exposure. The median relative dose intensity was 98% overall. The percentage of patients with a relative dose intensity >95% was 77%, 63%, and 71% across cohorts, respectively. Dose reductions occurred in 9% of patients, and the median duration of reduction was 97 days (range, 21-859 days). Dose interruptions occurred in 41% of patients, and the median duration of interruption was 10 days (range, 2-39 days).

AEs were consistent with those expected in a population of patients with advanced cGVHD receiving corticosteroid therapy. AEs reported in ≥20% of patients were upper respiratory infection (46%), diarrhea (33%), fatigue (33%), nausea (33%), increased liver function tests (33%), dyspnea (30%), headache (24%), peripheral edema (24%), cough (22%), and hypertension (20%) (Table 4). Serious AEs were reported in 43% of patients, and serious AEs reported in >1 patient were dyspnea (7%), lung infection (6%), hypoxia (4%), and influenza-like illness (4%). Sixty-one percent of patients had a grade≥3 AE, with the most common being dyspnea (13%), increased liver function tests (7%), hyperglycemia (7%), and hypoxia (7%) (Table 4). Grade≥3 cytopenias were reported in two patients (4%). These occurred at relapse of underlying malignancy in patients who had otherwise maintained normal blood counts during their belumosudil treatment.

continued belumosudil because of potentially drug-related AEs (cohort 1: diarrhea and headache; cohort 3: fatigue). Four patients, all in cohort 3, died during the study (secondary to relapse of leukemia, pneumonia (unknown pathogen), cardiac arrest, and cGVHD progression) with none of the deaths attributed to belumosudil. There was no dose response with respect to the observed AEs.

PD Analyses

In exploratory PD analyses of peripheral blood mononuclear cells across cohorts, the percentage of CD41 Tregs demonstrated an increasing trend early on by cycle 2 day 1 of belumosudil treatment. A simultaneous decrease in Th17 cells was also observed. The Th17 cells continued to decrease through C4D1 and C6D25. The percentage of CD41 Tregs continued to increase through C4D1 and C7D1, as shown in FIGS. 6A-6C. Because of the small sample size, correlative data with steroid dose were limited for any statistical analysis.

This study was the first to evaluate belumosudil treatment in human patients with cGVHD. All phenotypes of cGVHD, without requirements for inflammatory or fibrotic manifestations, were included. Patients with advanced multiorgan cGVHD treated with belumosudil achieved an ORR of 65%, with QOL improvements, corticosteroid dose reductions, and limited toxicity. With relatively small sample sizes, there was no difference in the ORR across cohorts.

Belumosudil achieved response rates that were meaningful and consistent across subgroups, including patients with severe cGVHD, patients who had received ≥2 prior systemic lines of therapy, patients who were refractory to their last lines of therapy before enrollment, and patients with ≥4 organs involved. The ORR among patients with nonsevere

TABLE 4

Safety Overview

| AE, No. (%) | Cohort 1 KD025 200 mg Once Daily (n = 17) | Cohort 2 KD025 200 mg Twice a Day (n = 16) | Cohort 3 KD025 400 mg Once Daily (n = 21) | Total (N = 54) |
| --- | --- | --- | --- | --- |
| Any AE | 17 (100) | 16 (100) | 16 (100) | 53 (98) |
| Grade ≥3 AE | 9 (53) | 10 (63) | 14 (67) | 33 (61) |
| Drug-related AE | 8 (47) | 8 (50) | 14 (67) | 30 (56) |
| SAE | 5 (29) | 6 (38) | 12 (57) | 23 (43) |
| Death | 0 | 0 | 2 (10) | 2 (4) |
| Drug-related SAE | 0 | 0 | 0 | 0 |
| All grade in ≥20% | | | | |
| URI | 9 (53) | 9 (56) | 7 (33) | 25 (46) |
| Diarrhea | 6 (35) | 5 (31) | 7 (33) | 18 (33) |
| Nausea | 6 (35) | 4 (25) | 8 (38) | 18 (33) |
| Fatigue | 6 (35) | 3 (19) | 9 (43) | 18 (33) |
| ALT/AST increased | 11 (65) | 5 (31) | 2 (10) | 18 (33) |
| Dyspnea | 3 (18) | 6 (38) | 7 (33) | 16 (30) |
| Peripheral edema | 3 (18) | 4 (25) | 6 (29) | 13 (24) |
| Headache | 4 (24) | 3 (19) | 6 (29) | 13 (24) |
| Cough | 1 (6) | 4 (25) | 7 (33) | 12 (22) |
| Hypertension | 5 (29) | 2 (13) | 4 (19) | 11 (20) |
| Grade ≥3 in ≥5% | | | | |
| Dyspnea | 1 (6) | 2 (13) | 4 (19) | 7 (13) |
| Lung infection or pneumonia | 1 (6) | 2 (13) | 2 (10) | 5 (9) |
| ALT/AST increased | 2 (12) | 2 (13) | 0 | 4 (7) |
| Hyperglycemia | 2 (12) | 0 | 2 (10) | 4 (7) |
| Hypoxia | 1 (6) | 1 (6) | 2 (10) | 4 (7) |
| Anemia | 2 (12) | 1 (6) | 0 | 3 (6) |

Abbreviations: AE, adverse event; SAE, serious adverse event; URI, upper respiratory tract infection.

No cases of cytomegalovirus (CMV) infection or reactivation were reported with belumosudil. Three patients discGVHD was 83%, suggesting that further studies of how belumosudil may benefit patients earlier in their disease are indicated. All responses at the patient level were PR; no CR was achieved. However, given the severity and extent of fibrotic cGVHD manifestations in this patient population, achieving CR in all organs was not expected, as some advanced fibrotic changes in the eyes, mouth, lungs, or joints and/or fascia can be irreversible. CR was observed in all organs except the lungs, where PR was achieved.

Belumosudil response kinetics suggest that most responders achieved responses rapidly within 8 weeks after receiving belumosudil. Belumosudil was well-tolerated, with a median DOR of 35 weeks across all responders. The ability to stay on therapy is dependent on the safety and long-term tolerability profile of the intervention. The median treatment duration was 8 months (range, 1-39 months). Twenty-eight percent of patients remained on belumosudil for >18 months. There was no reported CMV infection or reactivation, despite 57% of patients being CMV seropositive. The incidence of TEAEs and grade≥3TEAEs was similar across cohorts. The combination of well-tolerated therapy and efficacy in inducing responses translated into a 2-year OS rate of 82%, a median TTNT of 14 months, and FFS rates of 76% and 47% at 6 and 12 months, respectively.

In a prospective study conducted by the cGVHD Consortium, the 12-month FFS rate with response (CR/PR) after first-line therapy was 12% to 15%. (Martin P J, Storer B E, Inamoto Y, et al: An endpoint associated with clinical benefit after initial treatment for chronic graft-versus-host disease. Blood 130:360-367, 2017) In this study (after 1-3 prior lines of therapy), the 12-month FFS rate with response was 24%.

In the study of the present example, Belumosudil therapy was associated with a corticosteroid-sparing effect. The current treatment paradigm relies on corticosteroids as the mainstay of therapy; however, the related long-term toxicities mandate the use of the lowest possible dose or discontinuation whenever possible. The use of corticosteroid therapy is tied to quality of life, as the side effect profile of corticosteroid therapy contributes to patient symptom burden. Corticosteroid dose reduction was observed across both responders and nonresponders to belumosudil. Approximately 20% of patients were able to discontinue corticosteroid therapy during belumosudil treatment. Even in the absence of an NIH-defined response, patients experienced clinical benefit, as evidenced by improvements in LSS score or reductions in corticosteroid doses.

In this study, responses were achieved in patients with fibrotic manifestations in the lungs, joints and/or fascia, and eyes. These responses were observed in some cases after 24 weeks of treatment, further highlighting the benefits of sustaining effective therapy to achieve clinical benefit, particularly in patients with difficult-to-treat disease. Because the lower belumosudil 200-mg once daily dose was equally safe and effective, it has been further compared in the study described in Example 2 against the 200-mg twice a day dose for assessing dose recommendations.

Example 2: A Phase II Randomized Study of Belumosudil

The study of this Example 2 was a randomized, open-label, multicenter study of belumosudil mesylate for treatment of patients with chronic GVHD who had received 2 to 5 prior lines of systemic therapy and required additional treatment. Patients were excluded from the studies if platelets were <50×10$^9$/L; absolute neutrophil count<1.5×10$^9$/L; AST or ALT>3×ULN; total bilirubin>1.5×ULN; QTc(F) >480 ms; eGFR<30 mL/min/1.73 m 2; or FEV1≤39%. There were 66 patients treated with REZUROCK 200 mg taken orally once daily. Concomitant treatment with supportive care therapies for chronic GVHD was permitted. Concomitant treatment with GVHD prophylaxis and standard care systemic chronic GVHD therapies was permitted as long as the subject has been on a stable dose for at least 2 weeks prior to study. Initiation of new systemic chronic GVHD therapy while on study was not permitted.

Subject Eligibility

Eligible subjects were allogeneic hematopoietic cell transplant recipients aged ≥12 years with persistent cGVHD manifestations after receiving 2 to 5 prior systemic lines of therapy. Subjects were required to be receiving stable corticosteroid therapy for 2 weeks prior to screening and to have a Karnofsky or Lansky Performance Status Scale score≥60. Certain concurrent immunosuppressive medications were allowed because drug-drug interactions were not anticipated. Subjects were excluded if they had a relapse of their underlying malignancy, had a forced expiratory volume in 1 second (FEV1)≤39% or an NIH lung symptom score of 3, had developed posttransplant lymphoproliferative disease, had liver transaminases (aspartate aminotransferase [AST] or alanine transaminase [ALT])>3 times the upper limit of normal, had a total bilirubin>1.5 times the upper limit of normal for any reason, or were currently receiving ibrutinib.

Study Design and Treatment

Figure 7:
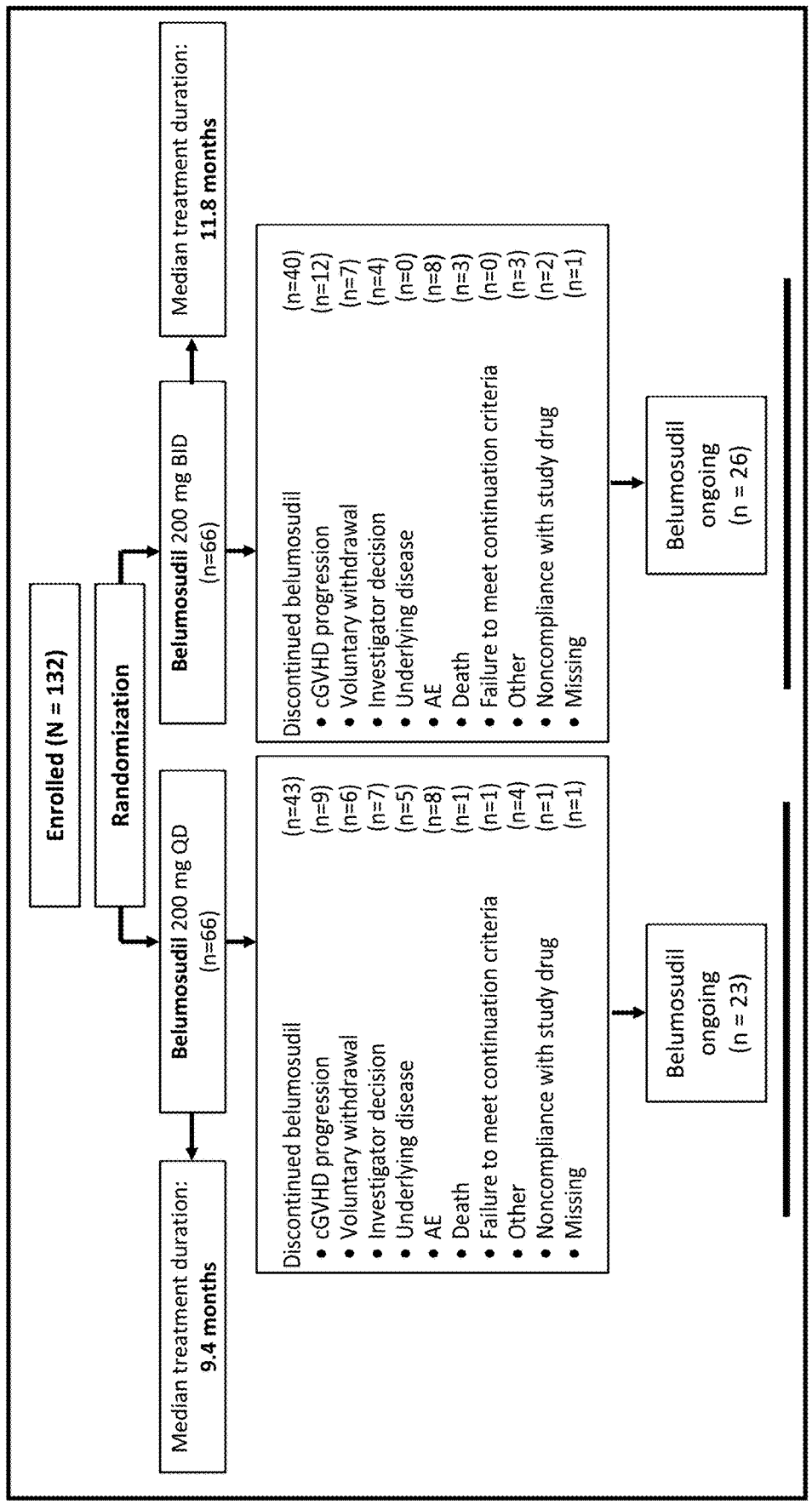
FIG. 7 is the CONSORT flow diagram describing the phase II randomized study of belumosudil of Example 2.

Screening for eligibility was conducted within 14 days of cycle 1 day 1. Treatment consisted of belumosudil 200 mg daily (Arm A) or 200 mg twice daily (Arm B) administered orally in subjects with cGVHD (FIG. 7). Randomization was stratified (1:1) by cGVHD severity and prior exposure to ibrutinib. Belumosudil was administered continuously in 28-day treatment cycles until clinically significant progression of cGVHD or unacceptable toxicity. Progression was defined using an organ-specific cGVHD response assessment, as defined by the 2014 NIH Consensus Development Project on Criteria for Clinical Trials in cGVHD, referred to as the 2014 NIH Consensus Criteria. After ≥2 weeks on belumosudil, corticosteriod therapy could be tapered at the discretion of the investigator. Subjects who did not achieve a response after 12 cycles of belumosudil treatment should be withdrawn if in the Investigator's judgment there is no evidence of clinical benefit.

Study End Points

The primary end point was best ORR at any time, defined as the proportion of subjects who achieved complete response (CR) or partial response (PR) according to the 2014 NIH Consensus Criteria. All responses were assessed by the study site investigators. Secondary end points included duration of response (DOR), time to response, changes in LSS summary score, failure-free survival (FFS), corticosteroid dose reductions, and overall survival (OS). DOR was measured from the time of initial PR or CR until documented progression from best response of cGVHD, time from initial response to start of additional systemic cGVHD therapy, or death. The 7-day LSS summary score was calculated based on the developer recommendations and was compared with the score from baseline; an improvement ≥7 points was considered clinically meaningful. FFS was defined as the interval between the start of belumosudil and the addition of a new cGVHD therapy, relapse, or NRM. The safety of belumosudil was evaluated by adverse event (AE) and serious AE (SAE) assessments. Relative dose intensity (RDI) was used as a surrogate measure of drug tolerability and was defined as actual dose intensity/planned dose intensity, where dose intensity was defined as the cumulative dose over the duration of exposure (mg/d). Actual dose intensity captured the sum of actual doses received over the duration of exposure and incorporated dose reductions and/or interruptions.

Statistical Analysis

The sample size was based on the primary efficacy end point (best ORR), with 1 planned interim analysis and a target ORR of 55%. With a target sample size of 63 subjects per treatment arm and an estimated 10% dropout rate, each treatment arm was estimated to have about 90% power to yield a 95% confidence interval (CI) of ORR that excluded 30% as the lower bound. Based on consultation with key opinion leaders, a 30% ORR was considered clinically meaningful in this heavily pretreated population with cGVHD and unmet medical needs. The Hochberg procedure was used for multiplicity adjustment for the primary end point of best ORR. The primary analysis was conducted using the modified intent-to-treat (mITT) population, defined as randomized subjects who received ≥1 dose of belumosudil. Interim, primary, and follow-up analyses were planned at about 2, 6, and 12 months, respectively, after 126 subjects were enrolled in the mITT population. Here, we report data from the 12-month analysis. CI was calculated using the Clopper-Pearson interval (exact) method.

Results

Subject Characteristics

A total of 132 subjects were enrolled in the clinical study. Overall, baseline demographics and clinical characteristics were comparable across treatment arms (Table 5) At enrollment, the median subject age was 56 years (range, 21-77). The median time from cGVHD diagnosis to enrollment was 28 months (range, 2-162). Thirty-one percent of subjects had moderate cGVHD at screening, and 67% had severe cGVHD, based on the 2014 NIH Consensus Criteria; 52% had involvement of ≥4 organs. Thirty-six percent of subjects had lung involvement at baseline, with 38% of these subjects having an NIH lung symptom score of 2. Subjects were previously treated with a median of 3 systemic lines of therapy. Seventy-two percent of subjects (n=79) had cGVHD refractory to their last systemic lines of therapy, 34% (n=45) had previously received ibrutinib, 29% (n=38) had previously received ruxolitinib, and 72% (n=95) had received ≥3 prior lines of therapy. The baseline median corticosteroid dose was 0.2 mg/kg per day (range, 0.03-1.07) of prednisone equivalent. The baseline mean corticosteroid dose was 0.25 mg/kg per day (range, 0.03-1.07) of prednisone equivalent.

TABLE 5

Baseline demographics and clinical characteristics

| Characteristic | Belumosudil, 200 mg daily (n = 66)** | Belumosudil 200 mg twice daily (n = 66) | Total (N = 132) |
| --- | --- | --- | --- |
| Age, median (range), y | 53 (21-77) | 57 (21-77) | 56 (21-77) |
| Males | 42 (64) | 33 (50) | 75 (57) |
| Indication for transplant | | | |
| AML | 28 (42) | 25 (38) | 53 (40) |
| ALL | 7 (11) | 12 (18) | 19 (14) |
| MDS | 8 (12) | 5 (8) | 13 (10) |
| CML | 5 (8) | 3 (5) | 8 (6) |
| Myelofibrosis | 3 (5) | 2 (3) | 5 (4) |
| CLL | 2 (3) | 2 (3) | 4 (3) |
| Non-Hodgkin lymphoma and DLBCL | 3 (5) | 4 (7) | 7 (5) |
| Other | 7 (11) | 11 (17) | 18 (14) |
| Conditioning intensity | | | |
| Myeloablative | 41 (62) | 42 (64) | 83 (63) |
| Nonmyeloablative | 22 (33) | 22 (33) | 44 (33) |
| Unknown | 3 (5) | 2 (3) | 5 (4) |
| Stem cell source | | | |
| Peripheral blood | 57 (86) | 63 (96) | 120 (91) |
| Bone marrow | 6 (9) | 3 (5) | 9 (7) |
| Cord blood | 0 | 0 | 0 |
| Unknown | 3 (5) | 0 | 3 (2) |
| HLA matching of donor/recipient | | | |
| Matched | 57 (86) | 62 (94) | 119 (90) |
| Partially matched | 8 (12) | 3 (5) | 11 (8) |
| Unknown | 0 | 1 (2) | 1 (1) |
| Missing | 1 (2) | 0 | 1 (1) |
| CMV-positive serostatus (donor/recipient) | | | |
| +/+ | 23 (35) | 16 (24) | 39 (30) |
| i) +/− | 3 (5) | 8 (12) | 11 (8) |
| ii) −/+− | 18 (27) | 17 (26) | 35 (27) |
| iii) −/− | 13 (20) | 16 (24) | 29 (22) |

TABLE 5-continued

Baseline demographics and clinical characteristics

| Characteristic | Belumosudil, 200 mg daily (n = 66)** | Belumosudil 200 mg twice daily (n = 66) | Total (N = 132) |
|---|---|---|---|
| 1 unknown | 3 (5) | 3 (5) | 6 (5) |
| Unknown/unknown | 5 (8) | 6 (9) | 11 (8) |
| Missing | 1 (2) | 0 | 1 (1) |
| iv) Time from cGVHD diagnosis to enrollment, median (range), mo | 25 (2-162) | 30 (4-144) | 29 (2-162) |
| NIH cGVHD severity* | | | |
| Severe | 46 (70) | 43 (65) | 89 (67) |
| Moderate | 18 (27) | 23 (35) | 41 (31) |
| Mild | 2 (3) | 0 | 2 (2) |
| Organ involvement | | | |
| No. of organs involved, median (range) | 4 (0-7) | 4 (2-7) | 4 (0-7) |
| ≥4 organs involved | 33 (50) | 35 (53) | 68 (52) |
| Skin | 55 (83) | 55 (83) | 110 (83) |
| Joints/fascia | 51 (77) | 49 (74) | 100 (76) |
| Eyes | 48 (73) | 49 (74) | 97 (74) |
| Mouth | 30 (46) | 42 (64) | 42 (64) |
| Lungs | 24 (36) | 23 (35) | 47 (36) |
| Esophagus | 19 (29) | 12 (18) | 31 (24) |
| Upper GI | 13 (20) | 10 (15) | 23 (17) |
| Lower GI | 6 (9) | 7 (11) | 13 (10) |
| Liver | 9 (14) | 4 (6) | 13 (10) |
| Baseline global severity rating | | | |
| 0 | 1 (2) | 0 | 1 (1) |
| 1 | 0 | 0 | 0 |
| 2 | 2 (3) | 1 (2) | 3 (2) |
| 3 | 3 (5) | 2 (3) | 5 (4) |
| 4 | 8 (12) | 3 (5) | 11 (8) |
| 5 | 6 (9) | 8 (12) | 14 (11) |
| 6 | 12 (18) | 14 (21) | 26 (20) |
| 7 | 11 (17) | 20 (30) | 31 (24) |
| 8 | 19 (29) | 14 (21) | 33 (25) |
| 9 | 4 (6) | 3 (5) | 7 (5) |
| 10 | 0 | 1 (2) | 1 (1) |
| Median Karnofsky Performance Status | | | |
| 60-70 | 10 (15) | 19 (29) | 29 (22) |
| 80-90 | 52 (79) | 43 (65) | 95 (72) |
| 100 | 4 (6) | 4 (6) | 8 (6) |
| Prior therapy characteristics | | | |
| Median prior LOTs, n | 3 | 4 | 3 |
| 2 prior LOTs | 23 (35) | 14 (21) | 37 (28) |
| 3 prior LOTs | 13 (20) | 17 (26) | 30 (23) |
| 4 prior LOTs | 15 (23) | 14 (21) | 29 (22) |
| 5 prior LOTs | 14 (21) | 19 (29) | 33 (25) |
| ≥6 prior LOTs | 1 (2) | 2 (3) | 3 (2) |
| Refractory to prior LOT | 44 (79) | 35 (65) | 79 (72) |
| Prior systemic cGVHD therapy type | | | |
| CS (prednisone) | 65 (99) | 65 (99) | 130 (99) |
| Tacrolimus | 40 (61) | 42 (64) | 82 (62) |
| ECP | 31 (47) | 32 (49) | 63 (48) |
| Sirolimus | 29 (44) | 33 (50) | 62 (47) |
| Ibrutinib | 22 (33) | 23 (35) | 45 (34) |
| Ruxolitinib | 20 (30) | 18 (27) | 38 (29) |
| MMF | 18 (27) | 15 (23) | 33 (25) |
| Rituximab | 15 (23) | 13 (20) | 28 (21) |
| MTX | 3 (5) | 3 (5) | 6 (5) |
| Cyclosporine | 4 (6) | 3 (5) | 5 (4) |

TABLE 5-continued

Baseline demographics and clinical characteristics

| Characteristic | Belumosudil, 200 mg daily (n = 66)** | Belumosudil 200 mg twice daily (n = 66) | Total (N = 132) |
|---|---|---|---|
| Imatinib | 3 (5) | 1 (2) | 4 (3) |
| Ixazomib | 0 | 1 (2) | 1 (1) |
| Ofatumumab | 0 | 1 (2) | 1 (1) |
| Concomitant systemic cGVHD therapy type† | | | |
| CS | 65 (99) | 66 (100) | 131 (99) |
| CNI | 24 (36) | 25 (38) | 49 (37) |
| ECP | 17 (26) | 22 (33) | 39 (30) |
| Sirolimus | 17 (26) | 18 (27) | 35 (27) |
| MMF | 11 (17) | 2 (3) | 13 (10) |
| Imatinib | 1 (2) | 1 (2) | 2 (2) |
| Rituximab | 1 (2) | 0 | 1 (1) |
| Ruxolitinib | 1 (2) | 0 | 1 (1) |
| Other systemic cGVHD therapies | 9 (14) | 13 (20) | 22 (17) |
| Prednisone-equivalent dose at enrollment, median (range), mg/kg/d | 0.20 (0.03-0.95) | 0.20 (0.03-1.07) | 0.20 (0.03-1.07) |

Unless otherwise noted, data are n (%). Percentages may not add to 100% because of rounding.
ALL, acute lymphocytic leukemia; AML, acute myelogenous leukemia; CLL, chronic lymphocytic leukemia; CML, chronic myelogenous leukemia; CMV, cytomegalovirus; DLBCL, diffuse large B-cell lymphoma; GI, gastrointestinal; MDS, myelodysplastic syndrome; MMF, mycophenolate mofetil; MTX, methotrexate.
*Disease severity was determined using NIH Global Severity of cGVHD scoring.
†Classified as concomitant systemic cGVHD medications on cycle 1 day 1.
**One subject was determined to be unevaluable as not having qualifying symptoms of cGVHD at baseline; hence, the figures in Table 5 may be adjusted accordingly.

The CONSORT diagram (FIG. 7) shows subject disposition. The median duration of treatment was 10 months (range, 0.4-22.0), and the median follow-up was 14 months (range, 1-22). Forty-four percent of subjects had received treatment for ≥12 months. At the time of the data analysis, 37% of subjects continued to receive belumosudil. Reasons for discontinuation included progression of cGVHD (n=21), voluntary withdrawal (n=13), AEs (n=16), physician decision (n=11), progression of underlying malignancy (n=5), death due to underlying malignancy or disease progression (n=4), other (n=7), and nonadherence to study drug (n=3).

Efficacy

Figure 8:
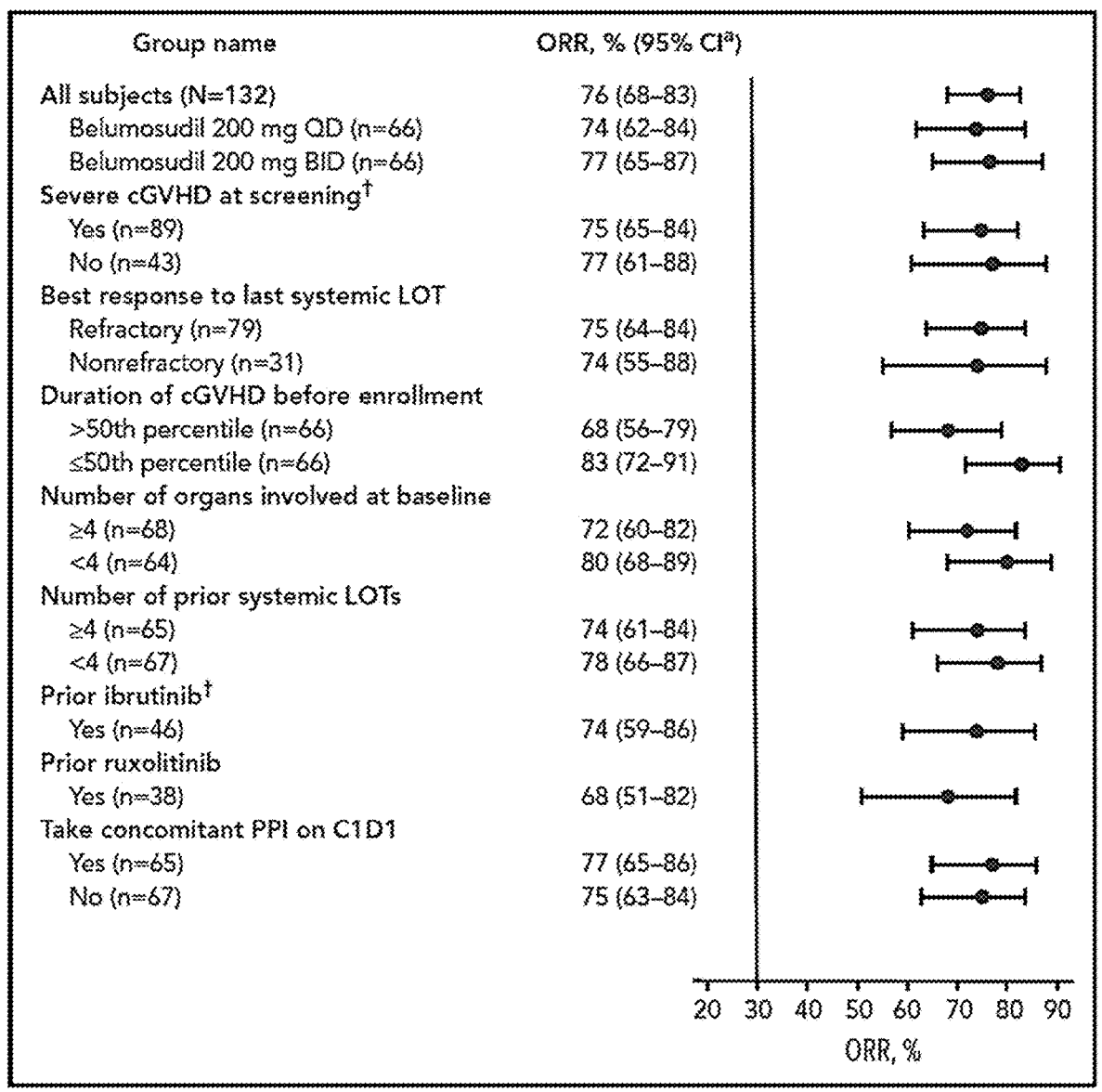
FIG. 8 is a forest plot of subgroup analyses of ORR (mITT). High ORRs were observed in all subgroups analyzed in the mITT population, and efficacy was maintained irrespective of prior treatments. The 50th percentile for duration of cGVHD before enrollment was 29 months. Response assessments performed on or after the initiation of a new systemic therapy for cGVHD were excluded from the analysis.

The best ORR for belumosudil 200 mg daily and 200 mg twice daily was 74% (95% CI, 62-84) and 77% (95% CI, 65-87), respectively (Table 6). High ORRs (61-85%) were observed in all subgroups (FIG. 8). Pooled responses across arms, unless stated otherwise. Efficacy of belumosudil was maintained, irrespective of prior ibrutinib (n=46) or ruxolitinib (n=38) therapy. The ORR for the subgroup with prior ruxolitinib therapy was 68% (95% CI, 51-83). The ORR (95% CI) for the subgroup with prior ibrutinib therapy was 74% (95% CI, 59-86).

TABLE 6

Efficacy end points in both arms within mITT population

| Efficacy end point | Belumosudil, 200 mg daily (n = 66)** | Belumosudil, 200 mg twice daily (n = 66) | Total (N = 132) |
|---|---|---|---|
| ORR | 49 (74) | 51 (77) | 100 (76) |
| 95% CI | 62-84 | 65-87 | 68-83 |
| ORR for responses occurring within 6 mo of treatment | 47 (71) | 48 (73) | 95 (72) |
| 95% CI | 59-82 | 60-83 | 64-80 |
| CR | 2 (3) | 1 (2) | 3 (2) |
| PR | 45 (68) | 47 (71) | 92 (70) |
| ORR for responses occurring within 12 mo of treatment | 49 (74) | 50 (76) | 99 (75) |
| 95% CI | 62-84 | 64-86 | 67-82 |
| CR | 4 (6) | 2 (3) | 6 (5) |
| PR | 45 (68) | 48 (73) | 93 (71) |
| Clinically significant improvement from baseline (LSS)* | | | |
| Overall | 39 (59) | 41 (62) | 80 (61) |
| Responder, n/N (%) | 34/49 (69) | 36/51 (71) | 70/100 (70) |
| Nonresponder, n/N (%) | 5/17 (29) | 5/15 (33) | 10/32 (31) |
| FFS at 6 mo (95% CI), % | 73 (61-83) | 76 (63-84) | 75 (66-81) |
| FFS at 12 mo (95% CI), % | 57 (44-68) | 56 (43-67) | 56 (47-64) |

TABLE 6-continued

Efficacy end points in both arms within mITT population

| Efficacy end point | Belumosudil, 200 mg daily (n = 66)** | Belumosudil, 200 mg twice daily (n = 66) | Total (N = 132) |
|---|---|---|---|
| Proportion with CS reduction | 42 (64) | 44 (67) | 86 (65) |
| Median CS reduction from baseline to greatest reduction, % | 38 | 50 | 50 |
| Mean change in CS dose from baseline, % | | | |
| Overall | −43 | −48 | −45 |
| Responder | −49 | −58 | −54 |
| Nonresponder | −22 | −10 | −16 |
| CS discontinuation | 13 (20) | 15 (23) | 28 21) |

Unless otherwise noted, data are n (%).
*Changes in cGVHD symptom burden were measured using LSS. Clinically meaningful improvement in symptom burden was defined as a decrease ≥7 points in LSS score.
**One subject was determined to be unevaluable as not having qualifying symptoms of cGVHD at baseline; hence, the figures in Table 6 may be adjusted accordingly.

Figure 9:
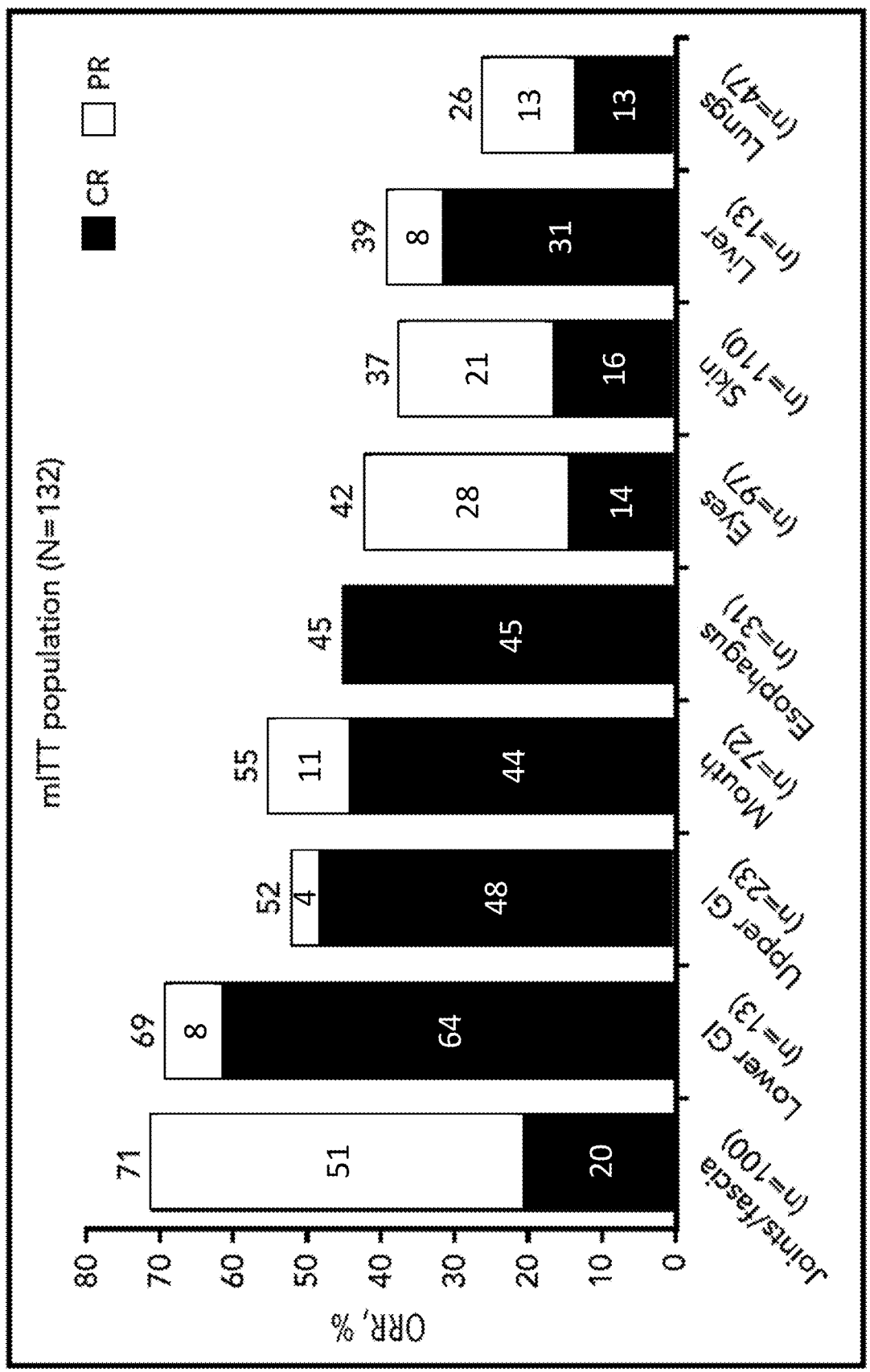
FIG. 9 describes ORR by organ system in the mITT population. Organ-specific analyses in the mITT population demonstrated ORRs in the skin, eyes, mouth, liver, lungs, joints/fascia, upper GI tract, lower GI tract, and esophagus. CR was seen across all affected organs.

Best ORR, including CR, was evaluated across all affected organs. In the mITT population, organ-specific analyses demonstrated a best ORR of 37% in the skin, 42% in the eyes, 55% in the mouth, 39% in the liver, 26% in the lungs, 71% in the joints/fascia, 52% in the upper gastrointestinal (GI) tract, 69% in the lower GI tract, and 45% in the esophagus (FIG. 9; Table 7). Overall, 7 subjects achieved CR in all affected organs. Of the 12 subjects with lung responses, 3 were scored as CR based on normalization of FEV1 (median increase, 23%; range, 18-25), with an additional 3 CRs based on a reduction in NIH lung symptom score from 1 to 0 in the absence of pulmonary function tests. Six additional subjects had PR, with a ≥10% increase in FEV1 (median increase for all subjects achieving PR, 10%; range, 0-15) or a reduction in NIH lung symptom score of 1 point when pulmonary function tests were unavailable. Of the 41 subjects with skin responses, 11 had a decrease in sclerotic features, 15 had a decrease in body surface area involvement, and 13 had improvements in body surface area involvement and sclerotic features. Two subjects had skin responses according to the investigator's clinical assessment, not according to the 2014 NIH Consensus Criteria.

TABLE 7

Summary of ORR by dose and organ system

| Organ system, n (%) | Belumosudil, 200 mg QD (n = 66)** | Belumosudil, 200 mg BID (n = 66) | Total (N = 132) |
|---|---|---|---|
| Joints and fascia | 51 (77) | 49 (74) | 100 (76) |
| CR | 10 (20) | 10 (20) | 20 (20) |
| PR | 28 (55) | 23 (47) | 51 (51) |
| ORR | 38 (75) | 33 (67) | 71 (71) |
| Lower GI | 6 (9) | 7 (11) | 13 (10) |
| CR | 4 (67) | 4 (57) | 8 (62) |
| PR | 0 | 1 (14) | 1 (8) |
| ORR | 4 (67) | 5 (71) | 9 (69) |
| Mouth | 30 (45) | 42 (64) | 72 (55) |
| CR | 15 (50) | 17 (41) | 32 (44) |
| PR | 1 (3) | 7 (17) | 8 (11) |
| ORR | 16 (53) | 24 (57) | 40 (56) |
| Upper GI | 13 (20) | 10 (15) | 23 (17) |
| CR | 7 (54) | 4 (40) | 11 (48) |
| PR | 1 (8) | 0 | 1 (4) |
| ORR | 8 (62) | 4 (40) | 12 (52) |
| Esophagus | 19 (29) | 12 (18) | 31 (23) |
| CR | 9 (47) | 5 (42) | 14 (45) |
| PR | 0 | 0 | 0 |
| ORR | 9 (47) | 5 (42) | 14 (45) |
| Eyes | 48 (73) | 49 (74) | 97 (73) |
| CR | 8 (17) | 6 (12) | 14 (14) |
| PR | 8 (17) | 19 (39) | 27 (28) |
| ORR | 16 (33) | 25 (51) | 41 (42) |
| Liver | 9 (14) | 4 (6) | 13 (10) |
| CR | 2 (22) | 2 (50) | 4 (31) |
| PR | 1 (11) | 0 | 1 (8) |
| ORR | 3 (33) | 2 (50) | 5 (39) |
| Skin | 55 (83) | 55 (83) | 110 (83) |
| CR | 8 (15) | 10 (18) | 18 (16) |
| PR | 10 (18) | 13 (24) | 23 (21) |
| ORR | 18 (33) | 23 (42) | 41 (37) |
| Lungs | 24 (36) | 23 (35) | 47 (36) |
| CR | 4 (17) | 2 (9) | 6 (13) |
| PR | 3 (13) | 3 (13) | 6 (13) |
| ORR | 7 (29) | 5 (22) | 12 (26) |

BID, twice a day; CR, complete response; GI, gastrointestinal; ORR, overall response rate; PR, partial response; QD, every day.
**One subject was determined to be unevaluable as not having qualifying symptoms of cGVHD at baseline; hence, the figures in Table 6 may be adjusted accordingly.

Figure 10A:
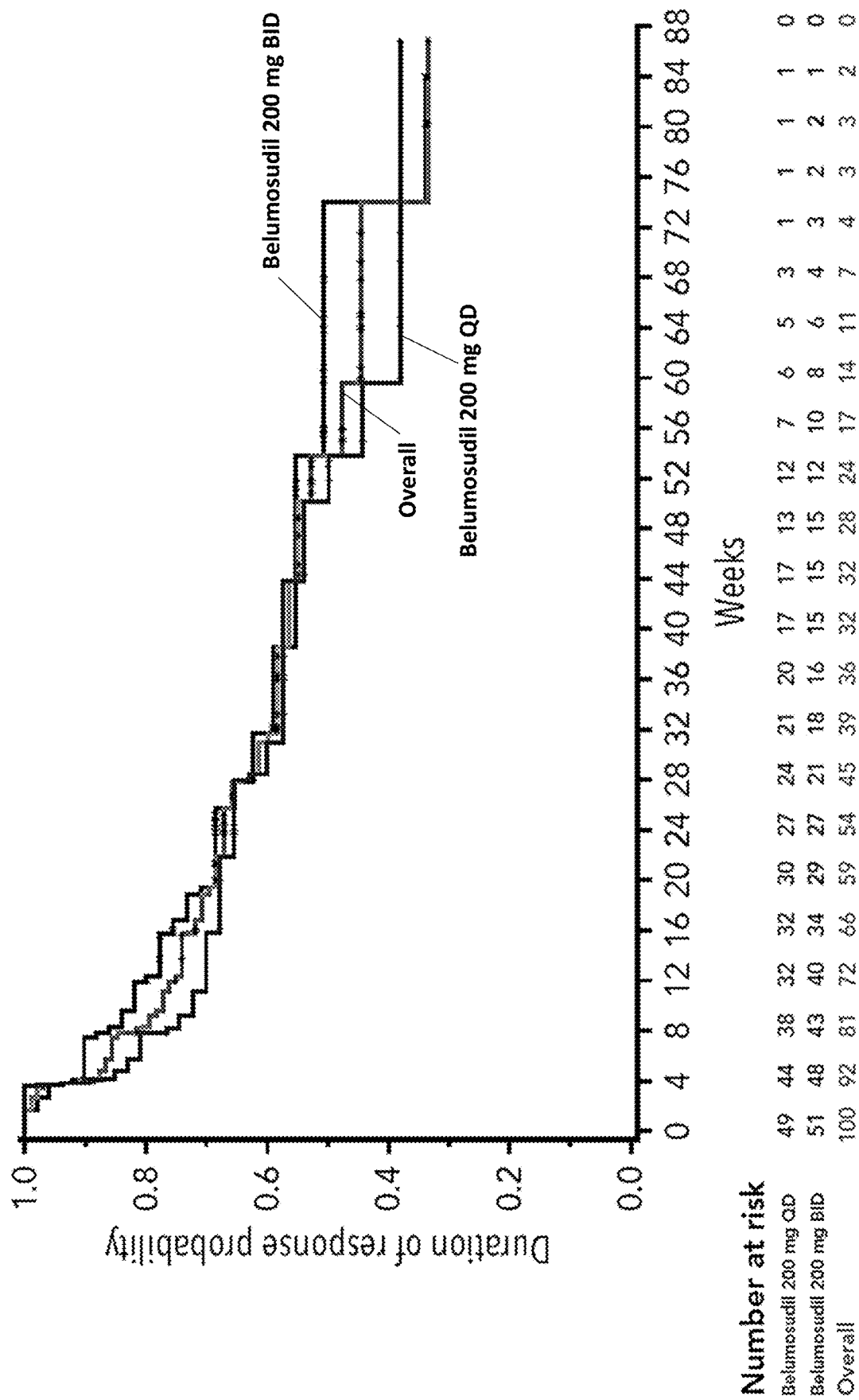
FIG. 10A describes durability of response to belumosudil by dose. Kaplan-Meier plot of DOR in the responder population. DOR was defined as the time from response until documented progression or start of another cGVHD systemic treatment; durability data continue to mature.
Figure 10B:
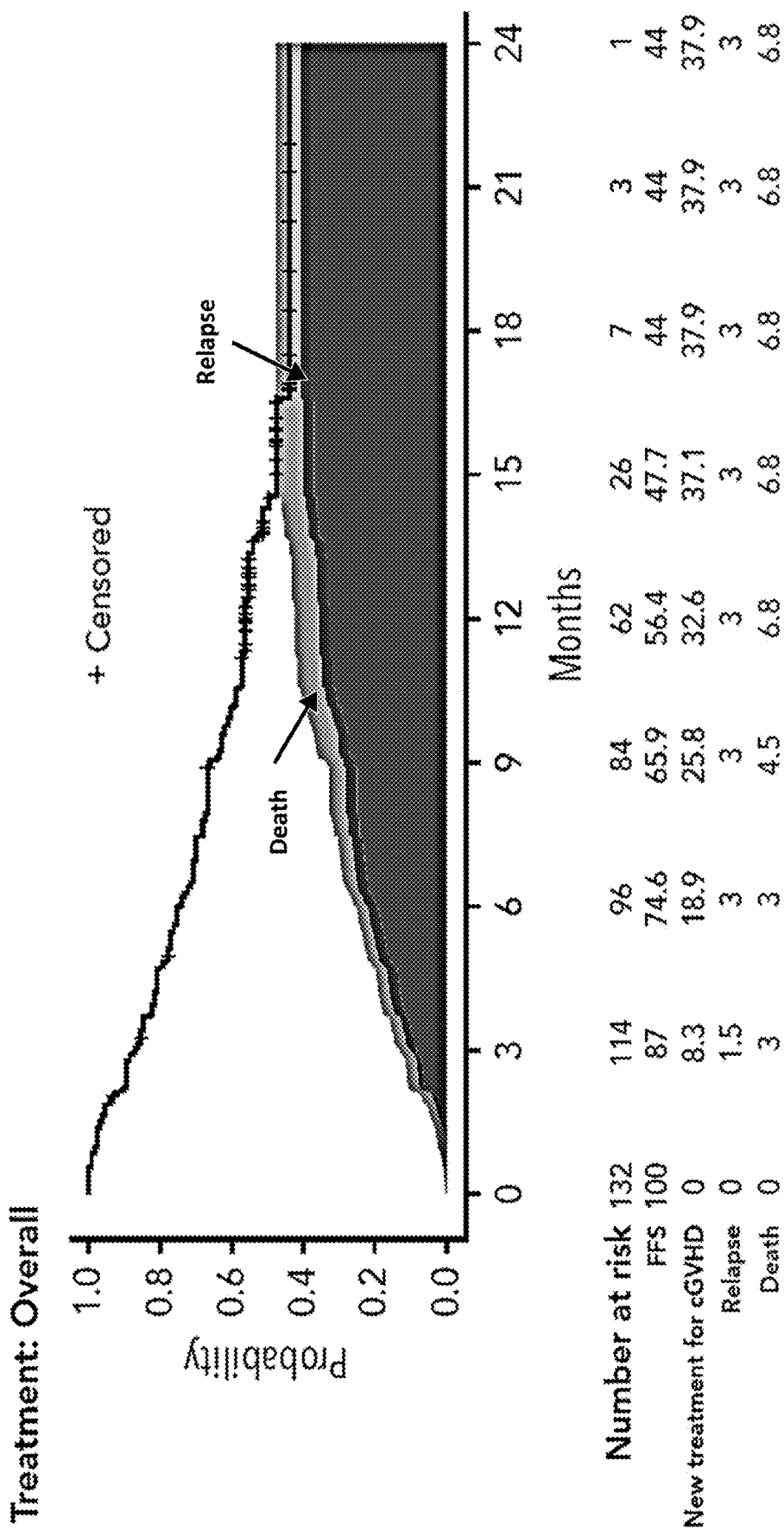
FIG. 10B describes durability of response to belumosudil by dose. Kaplan-Meier curves of estimated FFS in the mITT population, including reasons for failure. FFS was defined as the absence of cGVHD treatment change, NRM, and recurrent malignancy.
Figure 10C:
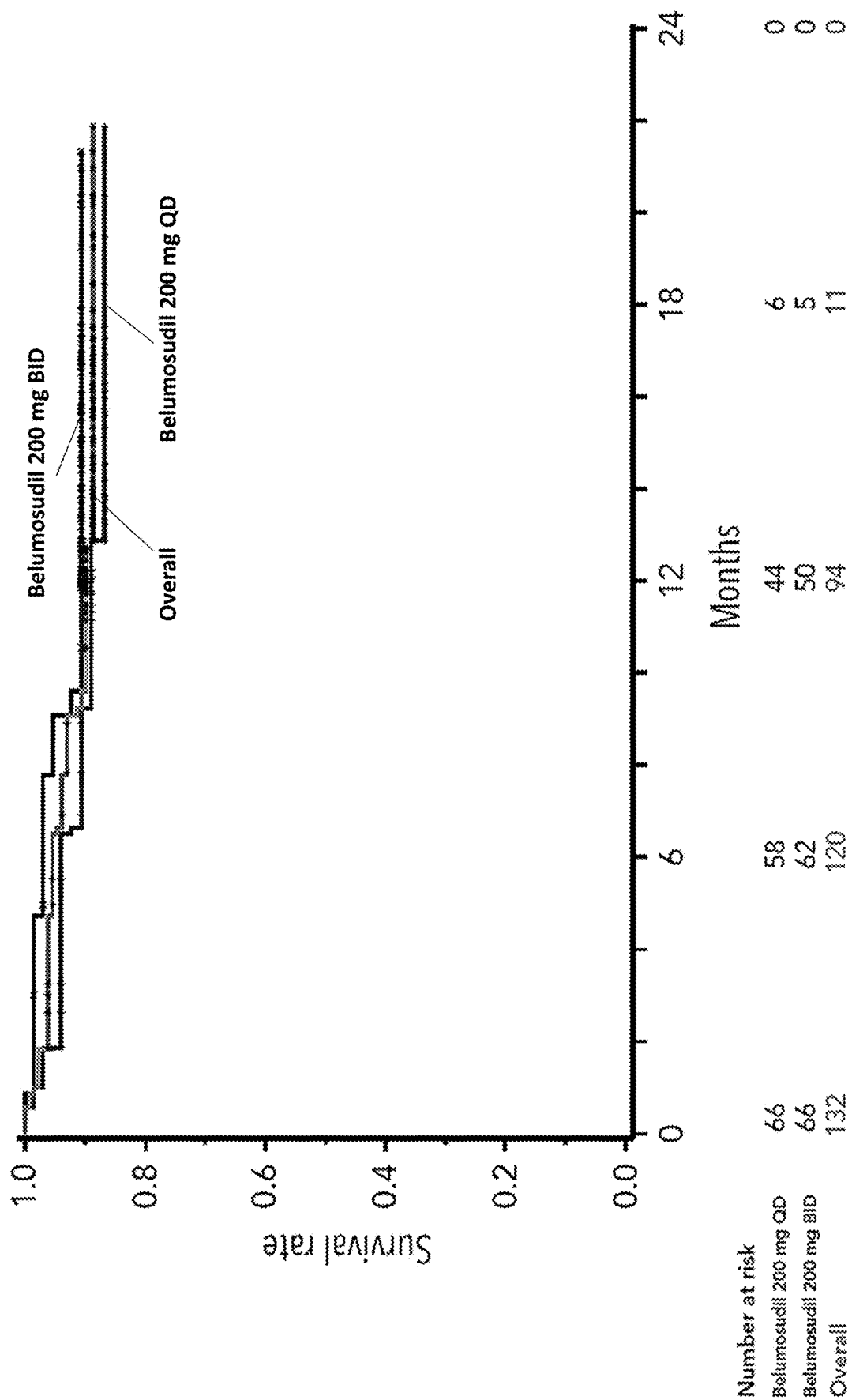
FIG. 10C describes durability of response to belumosudil by dose. Kaplan-Meier curves of estimated OS in the mITT population.
Figure 11:
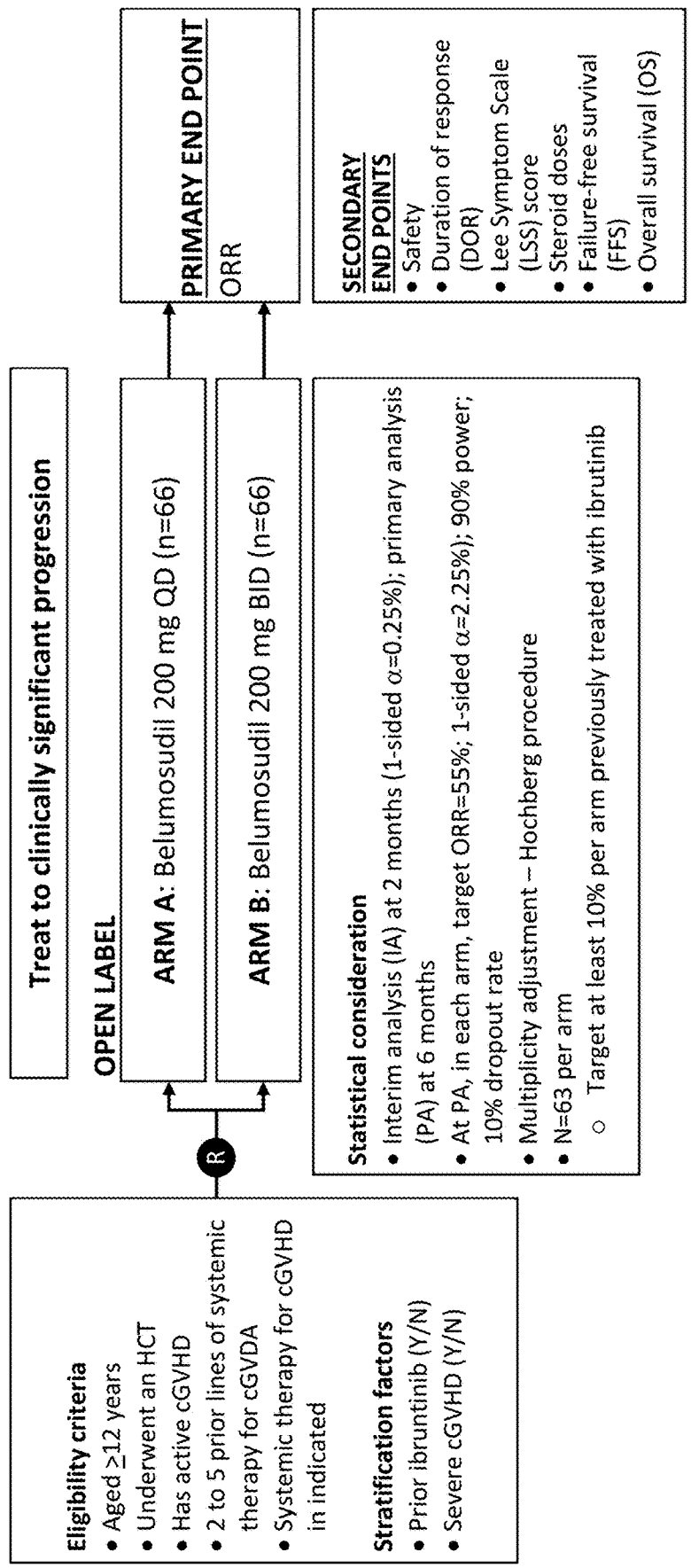
FIG. 11 describes the clinical study design of Example 2.

The overall median time to response was 5 weeks (range, 4-66) (FIG. 10A). Ninety-one percent of responses occurred within 6 months of treatment, with the remaining 9% of responses seen after 6 to 12 months of treatment. Fifty-nine percent of responders maintained responses for ≥20 weeks. The median DOR was 54 weeks in the responder population. The overall FFS rate was 75% (95% CI, 66-81) and 56% (95% CI, 47-64) at 6 and 12 months, respectively (FIG. 10B). Overall, low rates of nonrelapse mortality (NRM) (7%) and relapse (3%) were observed. The most common failure event was the initiation of a new systemic cGVHD therapy (38%). The 2-year OS rate was 89% (95% CI, 82-93) (FIG. 10C).

During treatment with belumosudil, 65% of subjects reduced their corticosteroid dose. The mean corticosteroid dose was reduced by 45% in the mITT population, with a mean corticosteroid dose reduction of 54% in responders. Twenty-one percent of subjects discontinued corticosteroid therapy. In addition, 22% of those subjects successfully discontinued calcineurin inhibitor (CNI) therapy, and 20% and 21% of subjects discontinued sirolimus and mycophenolate mofetil, respectively.

Clinically meaningful improvement (≥7-point reduction) in 7-day LSS summary score from baseline with belumosudil 200 mg daily and 200 mg twice daily was observed in 59% and 62% of them ITT population, respectively. This improvement was observed in 69% and 71% of responders in the belumosudil 200 mg daily and 200 mg twice-daily arms, respectively, as well as in 29% and 33% of nonresponders, respectively.

Safety

Belumosudil was well tolerated, with a median RDI of 99.7%. Eighty-one percent of subjects received an RDI>95%. AEs were consistent with those expected in patients with cGVHD receiving corticosteroid therapy and other immunosuppressive therapies (ISTs) (Table 8). Thirty eight percent of subjects had >1 SAE; the most common was pneumonia (7%). The most common (≥5%) grade 3 or 4 AEs were pneumonia (8%), hypertension (6%), and hyperglycemia (5%). Twenty-four percent of subjects had increased liver function tests (LFTs); at baseline, 5% of subjects had increased g-glutamyltransferase (GGT), 5% of subjects had increased AST, 3% of subjects had increased ALT, 3% of subjects had increased LFTs, and 1% of subjects had increased bilirubin. The most common liver-related AE was increased GGT (12%). Of the 83 subjects who discontinued treatment, 28 (21%) discontinued because of overall AEs, 16 (12%) discontinued because of possible drug-related AEs, 5 (4%) discontinued because of progression of underlying malignant disease, and 21 (16%) discontinued because of progression of cGVHD. Fourteen subjects died during the study; 2 from multiorgan failure and infection possibly related to belumosudil, 2 from cardiac arrest, 2 from respiratory failure, 1 from hemothorax resulting from lung biopsy, 1 from acute myeloid leukemia recurrence, and 6 during long-term follow-up (LTFU) (>28 days after last dose). Grade≥3 anemia was reported in 3% of subjects, neutropenia was reported in 2% of subjects, and thrombocytopenia was reported in 2% of subjects. There was 1 case of Epstein-Barr viremia that required treatment and 1 case of cytomegalovirus (CMV) reactivation; both were unrelated to belumosudil treatment.

TABLE 8

Safety overview

| AE | Belumosudil, 200 mg daily (n = 66)** | Belumosudil, 200 mg twice daily (n = 66) | Total (N = 132) |
|---|---|---|---|
| Any AE | 65 (99) | 66 (100) | 131 (99) |
| Grade ≥3 AEs | 37 (56) | 34 (52) | 71 (54) |
| Drug-related AEs | 49 (74) | 40 (61) | 89 (67) |
| SAEs | 27 (41) | 23 (35) | 50 (38) |
| Deaths* | 8 (12) | 6 (9) | 14 (11) |
| Drug-related SAEs | 5 (8) | 2 (3) | 7 (5) |
| All grades in ≥20% of subjects (overall) | | | |
| Fatigue | 30 (46) | 20 (30) | 50 (38) |
| Diarrhea | 23 (35) | 21 (32) | 44 (33) |
| Nausea | 23 (35) | 18 (27) | 41 (31) |
| Cough | 20 (30) | 17 (26) | 37 (28) |
| Upper respiratory tract infection | 17 (26) | 18 (27) | 35 (27) |
| Dyspnea | 21 (32) | 12 (18) | 33 (25) |
| Headache | 13 (20) | 18 (27) | 31 (24) |
| Peripheral edema | 17 (26) | 13 (20) | 30 (23) |
| Vomiting | 18 (27) | 10 (15) | 28 (21) |
| Muscle spasms | 13 (20) | 13 (20) | 26 (20) |
| Grade ≥3 in ≥5% of subjects in either arm | | | |
| Pneumonia | 6 (9) | 4 (6) | 10 (8) |
| Hypertension | 4 (6) | 4 (6) | 8 (6) |
| Hyperglycemia | 3 (5) | 3 (5) | 6 (5) |

TABLE 8-continued

Safety overview

| AE | Belumosudil, 200 mg daily (n = 66)** | Belumosudil, 200 mg twice daily (n = 66) | Total (N = 132) |
|---|---|---|---|
| Liver-related AEs | 12 (18) | 19 (29) | 31 (24) |
| GGT increased | 6 (9) | 10 (15) | 16 (12) |
| AST increased | 5 (8) | 8 (12) | 13 (10) |
| ALT increased | 4 (6) | 7 (11) | 11 (8) |
| Blood alkaline phosphatase increased | 4 (6) | 6 (9) | 10 (8) |
| Hypoalbuminemia | 2 (3) | 2 (3) | 4 (3) |
| Transaminases increased | 1 (2) | 1 (2) | 2 (2) |
| Bilirubin conjugated increased | 1 (2) | 0 | 1 (1) |
| LFT increased | 1 (2) | 0 | 1 (1) |

All data are n (%).
*Six subjects died during long-term follow-up (LTFU) (>28 days after last dose).
**One subject was determined to be unevaluable as not having qualifying symptoms of cGVHD at baseline; hence, the figures in Table 8 may be adjusted accordingly.

The study of the present Example 2 demonstrated promising efficacy and a favorable safety profile for belumosudil therapy in patients with steroid-refractory (SR) cGVHD. The study population, consisting of subjects with severe cGVHD with multiorgan involvement and fibrotic manifestations who were treated after a median of 3 prior systemic lines of therapy, achieved best ORRs of 74% and 77% in the 200-mg daily and 200-mg twice-daily treatment arms, respectively.

Responses to belumosudil were sustained and clinically meaningful, regardless of response to prior treatment, severity of cGVHD, and number of organs involved. Responses were observed in all organs, which was clinically significant because CR and PR were achieved in difficult-to-treat organs, such as the lungs and liver, as well as in organs with fibrotic manifestations, such as the skin. cGVHD greatly impairs quality of life, especially in patients with fibrotic multiorgan involvement, which can be challenging to treat. The CR and PR observed, along with improvements in LSS, limited interactions, and lack of drug toxicities, are promising results that demonstrate that belumosudil treatment may have the potential to improve overall patient well-being. Seven subjects achieved CR in all affected organs. CR in all affected organs can be difficult to achieve in cGVHD because of the irreversible changes that occur in several organs, most notably the eyes and the lungs. The clinical benefit and tolerability of belumosudil therapy demonstrate the potential to halt the expected cycling of therapies for cGVHD seen in clinical practice. Responses were sustained in 59% of responders for >20 weeks at the 12-month analysis. The median DOR was 54 weeks in responders at the 12-month analysis.

In a patient population that is vulnerable to AEs and infections from immunosuppressive therapy (IST), belumosudil was well tolerated, allowing most subjects to remain on therapy to achieve clinically meaningful results and improvement in quality of life, which could be maintained with continued treatment. Only 12% of subjects discontinued belumosudil because of possible drug-related AEs. The median duration of treatment was 10 months (range, 0.4-22.0), and 37% of subjects continued to receive belumosudil after this time point, AEs were manageable, with few grade≥3 SAEs attributable to belumosudil. The SAE rates were comparable between the two treatment arms. Many current cGVHD treatment options are immunosuppressive and, consequently, increase the risk of infection and may cause hematologic toxicities, including leukopenia, anemia, and thrombocytopenia. Grade≥3 cytopenias were present in <4% of subjects, and there was only one report of cytomegalovirus (CMV) reactivation that was unrelated to belumosudil treatment. Cytopenias and CMV infection present as serious complications of cGVHD and cGVHD therapeutics; thus, the low rates of grade≥3 cytopenias and CMV infection rates are promising features of the safety profile of belumosudil.

In the present study, all subjects received belumosudil. Requiring randomization to best available therapy was not deemed appropriate, because subjects had previously progressed following >2 systemic lines of therapy, where response rates were historically low. Indeed, subjects in this study had already attempted a median of three prior lines of best available therapy for cGVHD before enrollment, with the use of ECP (48%), ibrutinib (34%), ruxolitinib (29%), and rituximab (21%), among other agents. The best ORR was 75% in subjects who were refractory to their last lines of therapy.

Example 3: Risk Management for Side Effects

In the clinical studies in prior examples 1 and 2, 83 adult patients with chronic GVHD were treated with belumosudil 200 mg once daily. The median duration of treatment was 9.2 months (range 0.5 to 44.7 months). Fatal adverse reaction was reported in one patient with severe nausea, vomiting, diarrhea and multi-organ failure.

Fatal adverse reaction was reported in one patient with severe nausea, vomiting, diarrhea and multi-organ failure.

Permanent discontinuation of belumosudil due to adverse reactions occurred in 18% of patients. The adverse reactions which resulted in permanent discontinuation of belumosudil in >3% of patients included nausea (4%). Adverse reactions leading to dose interruption occurred in 29% of patients. The adverse reactions leading to dose interruption in ≥2% were infections (11%), diarrhea (4%), and asthenia, dyspnea, hemorrhage, hypotension, liver function test abnormal, nausea, pyrexia, edema, and renal failure with (2% each).

The most common (≥20%) adverse reactions, including laboratory abnormalities, were infections, asthenia, nausea, diarrhea, dyspnea, cough, edema, hemorrhage, abdominal pain, musculoskeletal pain, headache, phosphate decreased, gamma glutamyl transferase increased, lymphocytes decreased, and hypertension.

Table 9 summarizes the nonlaboratory adverse reactions.

TABLE 9

Nonlaboratory Adverse Reactions in ≥10% Patients with Chronic GVHD Treated with Belumosudil

| Adverse Reaction | Belumosudil 200 mg once daily (N = 83) | |
| --- | --- | --- |
| | All Grades (%) | Grades 3-4 (%) |
| Infections and infestations | | |
| Infection (pathogen not specified)[a] | 53 | 16 |
| Viral infection[b] | 19 | 4 |
| Bacterial infection[c] | 16 | 4 |
| General disorders and administration site conditions | | |
| Asthenia[d] | 46 | 4 |
| Edema[e] | 27 | 1 |
| Pyrexia | 18 | 1 |

TABLE 9-continued

Nonlaboratory Adverse Reactions in ≥10% Patients with Chronic GVHD Treated with Belumosudil

| Adverse Reaction | Belumosudil 200 mg once daily (N = 83) | |
| --- | --- | --- |
| | All Grades (%) | Grades 3-4 (%) |
| Gastrointestinal | | |
| Nausea[f] | 42 | 4 |
| Diarrhea | 35 | 5 |
| Abdominal pain[g] | 22 | 1 |
| Dysphagia | 16 | 0 |
| Respiratory, thoracic and mediastinal | | |
| Dyspnea[h] | 33 | 5 |
| Cough[i] | 30 | 0 |
| Nasal congestion | 12 | 0 |
| Vascular | | |
| Hemorrhage[j] | 23 | 5 |
| Hypertension | 21 | 7 |
| Musculoskeletal and connective tissue | | |
| Musculoskeletal pain[k] | 22 | 4 |
| Muscle spasm | 17 | 0 |
| Arthralgia | 15 | 2 |
| Nervous system | | |
| Headache[l] | 21 | 0 |
| Metabolism and nutrition | | |
| Decreased appetite | 17 | 1 |
| Skin and subcutaneous | | |
| Rash[m] | 12 | 0 |
| Pruritus[n] | 11 | 0 |

[a]infection with an unspecified pathogen includes acute sinusitis, device related infection, ear infection, folliculitis, gastroenteritis, gastrointestinal infection, hordeolum, infectious colitis, lung infection, skin infection, tooth infection, urinary tract infection, wound infection, upper respiratory tract infection, pneumonia, conjunctivitis, sinusitis, respiratory tract infection, bronchitis, sepsis, septic shock.
[b]includes influenza, rhinovirus infection, gastroenteritis viral, viral upper respiratory tract infection, bronchitis viral, Epstein-Barr viremia, Epstein-Barr virus infection, parainfluenzae virus infection, Varicella zoster virus infection, viral infection.
[c]includes cellulitis, Helicobacter infection, Staphylococcal bacteremia, catheter site cellulitis, Clostridium difficile colitis, *Escherichia* urinary tract infection, gastroenteritis *Escherichia coli*, Pseudomonas infection, urinary tract infection bacterial.
[d]includes fatigue, asthenia, malaise.
[e]includes edema peripheral, generalized edema, face edema, localized edema, edema.
[f]includes nausea, vomiting.
[g]includes abdominal pain, abdominal pain upper, abdominal pain lower.
[h]includes dyspnea, dyspnea exertional, apnea, orthopnea, sleep apnea syndrome.
[i]includes cough, productive cough.
[j]includes contusion, hematoma, epistaxis, increased tendency to bruise, conjunctival hemorrhage, hematochezia, mouth hemorrhage, catheter site hemorrhage, hematuria, hemothorax, purpura.
[k]includes pain in extremity, back pain, flank pain, limb discomfort, musculoskeletal chest pain, neck pain, musculoskeletal pain.
[l]includes headache, migraine.
[m]includes rash, rash maculo-papular, rash erythematous, rash generalized, dermatitis exfoliative.
[n]includes pruritus, pruritus generalized.

Table 10 summarizes the laboratory abnormalities in belumosudil.

TABLE 10

Selected Laboratory Abnormalities in Patients with Chronic GVHD Treated with Belumosudil.

| | Belumosudil 200 mg once daily | | |
| --- | --- | --- | --- |
| Parameter | Grade 0-1 Baseline (N) | Grade 2-4 Max Post (%) | Grade 3-4 Max Post (%) |
| Chemistry | | | |
| Phosphate Decreased | 76 | 28 | 7 |
| Gamma Glutamyl Transferase Increased | 47 | 21 | 11 |

TABLE 10-continued

Selected Laboratory Abnormalities in Patients
with Chronic GVHD Treated with Belumosudil.

| | Belumosudil 200 mg once daily | | |
|---|---|---|---|
| Parameter | Grade 0-1 Baseline (N) | Grade 2-4 Max Post (%) | Grade 3-4 Max Post (%) |
| Calcium Decreased | 82 | 12 | 1 |
| Alkaline Phosphatase Increased | 80 | 9 | 0 |
| Potassium Increased | 82 | 7 | 1 |
| Alanine Aminotransferase Increased | 83 | 7 | 2 |
| Creatinine Increased | 83 | 4 | 0 |
| Hematology | | | |
| Lymphocytes Decreased | 62 | 29 | 13 |
| Hemoglobin Decreased | 79 | 11 | 1 |
| Platelets Decreased | 82 | 10 | 5 |
| Neutrophil Count Decreased | 83 | 8 | 4 |

Table 11 summarizes recommended dosage modifications for Belumosudil for Adverse Reactions.

| Adverse Reaction | Severity* | REZUROCK Dosage Modifications |
|---|---|---|
| Hepatotoxicity [see Adverse Reactions (6.1)] | Grade 3 AST or ALT (5x to 20x ULN) or Grade 2 bilirubin (1.5x to 3x ULN) | Hold REZUROCK until recovery of bilirubin, AST and ALT to Grade 0-1, then resume REZUROCK at the recommended dose. |
| | Grade 4 AST or ALT (more than 20x ULN) or Grade ≥3 bilirubin (more than 3x ULN) | Discontinue REZUROCK permanently. |
| Other adverse reactions [see Adverse Reactions (6.1)] | Grade 3 | Hold REZUROCK until recovery to Grade 0-1, then resume REZUROCK at the recommended dose level. |
| | Grade 4 | Discontinue REZUROCK permanently. |

*Based on CTCAE v 4.03

Example 4: United States REZUROCK™ (Belumosudil) FDA Label

Indications and Usage

REZUROCK is a kinase inhibitor indicated for the treatment of adult and pediatric patients 12 years and older with chronic graft-versus-host disease (chronic GVHD) after failure of at least two prior lines of systemic therapy. (1)

Dosage and Administration

Recommended Dosage: 200 mg taken orally once daily with food. (2.1)

Dosage Forms and Strengths

Tablet: 200 mg. (3)

Contraindications

None. (4)

Warnings and Precautions

Embryo-Fetal Toxicity: Can cause fetal harm. Advise females of reproductive potential of the potential risk to a fetus and to use effective contraception. (5.1, 8.1, 8.3)

Drug Interactions

Strong CYP3A Inducers: Increase REZUROCK dosage to 200 mg twice daily. (7.1) Proton Pump Inhibitors: Increase REZUROCK dosage to 200 mg twice daily. (7.1)

Adverse Reactions

The most common (≥20%) adverse reactions, including laboratory abnormalities, were infections, asthenia, nausea, diarrhea, dyspnea, cough, edema, hemorrhage, abdominal pain, musculoskeletal pain, headache, phosphate decreased, gamma glutamyl transferase increased, lymphocytes decreased, and hypertension. (6.1)

Use in Specific Populations

Lactation: Advise not to breastfeed. (8.2)

See 17 for PATIENT COUNSELING INFORMATION and FDA-approved patient labeling.

Full Prescribing Information

1 Indications and Usage

REZUROCK is indicated for the treatment of adult and pediatric patients 12 years and older with chronic graft-versus-host disease (chronic GVHD) after failure of at least two prior lines of systemic therapy.

2 Dosage and Administration 2.1 Recommended Dosage

The recommended dose of REZUROCK is 200 mg given orally once daily until progression of chronic GVHD that requires new systemic therapy.

Instruct the patient on the following:

Swallow REZUROCK tablets whole. Do not cut, crush, or chew tablets.

Take REZUROCK with a meal at approximately the same time each day [see Clinical Pharmacology (12.3)].

If a dose of REZUROCK is missed, instruct the patient to not take extra doses to make up the missed dose.

Treatment with REZUROCK has not been studied in patients with pre-existing severe renal or hepatic impairment. For patients with pre-existing severe renal or hepatic impairment, consider the risks and potential benefits before initiating treatment with REZUROCK [see Clinical Pharmacology (12.3)].

2.2 Dose Modifications for Adverse Reactions

Monitor total bilirubin, aspartate aminotransferase (AST), and alanine aminotransferase (ALT) at least monthly. Modify the REZUROCK dosage for adverse reactions as per Table 12.

TABLE 12

Recommended Dosage Modifications for REZUROCK for Adverse Reactions

| Adverse Reaction | Severity* | REZUROCK Dosage Modifications |
|---|---|---|
| Hepatotoxicity [see Adverse Reactions (6.1)] | Grade 3 AST or ALT (5x to 20x ULN) or Grade 2 bilirubin (1.5x to 3x ULN) | Hold REZUROCK until recovery of bilirubin, AST and ALT to Grade 0-1, then resume REZUROCK at the recommended dose. |
| | Grade 4 AST or ALT (more than 20x ULN) or Grade ≥3 bilirubin (more than 3x ULN) | Discontinue REZUROCK permanently. |
| Other adverse reactions [see Adverse Reactions (6.1)] | Grade 3 | Hold REZUROCK until recovery to Grade 0-1, then resume REZUROCK at the recommended dose level. |
| | Grade 4 | Discontinue REZUROCK permanently. |

*Based on CTCAE v 4.03

2.3 Dosage Modification Due to Drug Interactions
Strong CYP3A Inducers

Increase the dosage of REZUROCK to 200 mg twice daily when coadministered with strong CYP3A inducers [see Drug Interactions (7.1)].

Proton Pump Inhibitors

Increase the dosage of REZUROCK to 200 mg twice daily when coadministered with proton pump inhibitors [see Drug Interactions (7.1)].

3 Dosage Forms and Strengths

Each 200 mg tablet is a pale yellow film-coated oblong tablet debossed with "KDM" on one side and "200" on the other side.

4 Contraindications

None.

5 Warnings and Precautions
5.1 Embryo-Fetal Toxicity

Based on findings in animals and its mechanism of action, REZUROCK can cause fetal harm when administered to a pregnant woman. In animal reproduction studies, administration of belumosudil to pregnant rats and rabbits during the period organogenesis caused adverse developmental outcomes including embryo-fetal mortality and malformations at maternal exposures (AUC) less than those in patients at the recommended dose. Advise pregnant women of the potential risk to a fetus. Advise females of reproductive potential and males with female partners of reproductive potential to use effective contraception during treatment with REZUROCK and for at least one week after the last dose [see Use in Specific Populations (8.1, 8.3), Nonclinical Toxicology (13.1)]

6 Adverse Reactions
6.1 Clinical Trial Experience

Because clinical trials are conducted under widely variable conditions, adverse reaction rates observed in clinical trials of a drug cannot be directly compared with rates of clinical trials of another drug and may not reflect the rates observed in practice.

Chronic Graft versus Host Disease

In two clinical trials (Study KD025-213 and Study KD025-208), 83 adult patients with chronic GVHD were treated with REZUROCK 200 mg once daily [see Clinical Studies (14.1)]. The median duration of treatment was 9.2 months (range 0.5 to 44.7 months).

Fatal adverse reaction was reported in one patient with severe nausea, vomiting, diarrhea and multi-organ failure.

Permanent discontinuation of REZUROCK due to adverse reactions occurred in 18% of patients. The adverse reactions which resulted in permanent discontinuation of REZUROCK in >3% of patients included nausea (4%). Adverse reactions leading to dose interruption occurred in 29% of patients. The adverse reactions leading to dose interruption in ≥2% were infections (11%), diarrhea (4%), and asthenia, dyspnea, hemorrhage, hypotension, liver function test abnormal, nausea, pyrexia, edema, and renal failure with (2% each).

The most common (≥20%) adverse reactions, including laboratory abnormalities, were infections, asthenia, nausea, diarrhea, dyspnea, cough, edema, hemorrhage, abdominal pain, musculoskeletal pain, headache, phosphate decreased, gamma glutamyl transferase increased, lymphocytes decreased, and hypertension.

Table 13 summarizes the nonlaboratory adverse reactions.

TABLE 13

Nonlaboratory Adverse Reactions in ≥10% Patients with Chronic GVHD Treated with REZUROCK

| | REZUROCK 200 mg once daily (N = 83) | |
|---|---|---|
| Adverse Reaction | All Grades (%) | Grades 3-4 (%) |
| Infections and infestations | | |
| Infection (pathogen not specified)[a] | 53 | 16 |
| Viral infection[b] | 19 | 4 |
| Bacterial infection[c] | 16 | 4 |
| General disorders and administration site conditions | | |
| Asthenia[d] | 46 | 4 |
| Edema[e] | 27 | 1 |
| Pyrexia | 18 | 1 |
| Gastrointestinal | | |
| Nausea[f] | 42 | 4 |
| Diarrhea | 35 | 5 |
| Abdominal pain[g] | 22 | 1 |
| Dysphagia | 16 | 0 |
| Respiratory, thoracic and mediastinal | | |
| Dyspnea[h] | 33 | 5 |
| Cough[i] | 30 | 0 |
| Nasal congestion | 12 | 0 |

TABLE 13-continued

Nonlaboratory Adverse Reactions in ≥10% Patients with Chronic GVHD Treated with REZUROCK

| Adverse Reaction | REZUROCK 200 mg once daily (N = 83) | |
|---|---|---|
|  | All Grades (%) | Grades 3-4 (%) |
| Vascular | | |
| Hemorrhage[j] | 23 | 5 |
| Hypertension | 21 | 7 |
| Musculoskeletal and connective tissue | | |
| Musculoskeletal pain[k] | 22 | 4 |
| Muscle spasm | 17 | 0 |
| Arthralgia | 15 | 2 |
| Nervous system | | |
| Headache[l] | 21 | 0 |
| Metabolism and nutrition | | |
| Decreased appetite | 17 | 1 |
| Skin and subcutaneous | | |
| Rash[m] | 12 | 0 |
| Pruritus[n] | 11 | 0 |

[a]infection with an unspecified pathogen includes acute sinusitis, device related infection, ear infection, folliculitis, gastroenteritis, gastrointestinal infection, hordeolum, infectious colitis, lung infection, skin infection, tooth infection, urinary tract infection, wound infection, upper respiratory tract infection, pneumonia, conjunctivitis, sinusitis, respiratory tract infection, bronchitis, sepsis, septic shock.
[b]includes influenza, rhinovirus infection, gastroenteritis viral, viral upper respiratory tract infection, bronchitis viral, Epstein-Barr viremia, Epstein-Barr virus infection, parainfluenzae virus infection, Varicella zoster virus infection, viral infection.
[c]includes cellulitis, Helicobacter infection, Staphylococcal bacteremia, catheter site cellulitis, Clostridium difficile colitis, Escherichia urinary tract infection, gastroenteritis Escherichia coli, Pseudomonas infection, urinary tract infection bacterial.
[d]includes fatigue, asthenia, malaise.
[e]includes edema peripheral, generalized edema, face edema, localized edema, edema.
[f]includes nausea, vomiting.
[g]includes abdominal pain, abdominal pain upper, abdominal pain lower.
[h]includes dyspnea, dyspnea exertional, apnea, orthopnea, sleep apnea syndrome.
[i]includes cough, productive cough.
[j]includes contusion, hematoma, epistaxis, increased tendency to bruise, conjunctival hemorrhage, hematochezia, mouth hemorrhage, catheter site hemorrhage, hematuria, hemothorax, purpura.
[k]includes pain in extremity, back pain, flank pain, limb discomfort, musculoskeletal chest pain, neck pain, musculoskeletal pain.
[l]includes headache, migraine.
[m]includes rash, rash maculo-papular, rash erythematous, rash generalized, dermatitis exfoliative.
[n]includes pruritus, pruritus generalized.

Table 14 summarizes the laboratory abnormalities in REZUROCK.

TABLE 14

Selected Laboratory Abnormalities in Patients with Chronic GVHD Treated with REZUROCK

| Parameter | REZUROCK 200 mg once daily | | |
|---|---|---|---|
|  | Grade 0-1 Baseline (N) | Grade 2-4 Max Post (%) | Grade 3-4 Max Post (%) |
| Chemistry | | | |
| Phosphate Decreased | 76 | 28 | 7 |
| Gamma Glutamyl Transferase Increased | 47 | 21 | 11 |
| Calcium Decreased | 82 | 12 | 1 |
| Alkaline Phosphatase Increased | 80 | 9 | 0 |
| Potassium Increased | 82 | 7 | 1 |
| Alanine Aminotransferase Increased | 83 | 7 | 2 |
| Creatinine Increased | 83 | 4 | 0 |
| Hematology | | | |
| Lymphocytes Decreased | 62 | 29 | 13 |
| Hemoglobin Decreased | 79 | 11 | 1 |
| Platelets Decreased | 82 | 10 | 5 |
| Neutrophil Count Decreased | 83 | 8 | 4 |

7 Drug Interactions
7.1 Effect of Other Drugs on REZUROCK
Strong CYP3A Inducers Coadministration of REZUROCK with strong CYP3A inducers decreases belumosudil exposure [see Clinical Pharmacology (12.3)], which may reduce the efficacy of REZUROCK. Increase the dosage of REZUROCK when coadministered with strong CYP3A inducers [see Dosage and Administration (2.3)].

Proton Pump Inhibitors

Coadministration of REZUROCK with proton pump inhibitors decreases belumosudil exposure [see Clinical Pharmacology (12.3)], which may reduce the efficacy of REZUROCK. Increase the dosage of REZUROCK when coadministered with proton pump inhibitors [see Dosage and Administration (2.3)].

8 Use in Specific Populations
8.1 Pregnancy
Risk Summary

Based on findings from animal studies and the mechanism of action [see Clinical Pharmacology (12.1)], REZUROCK can cause fetal harm when administered to pregnant women. There are no available human data on REZUROCK use in pregnant women to evaluate for a drug-associated risk. In animal reproduction studies, administration of belumosudil to pregnant rats and rabbits during the period of organogenesis resulted in adverse developmental outcomes, including alterations to growth, embryo-fetal mortality, and embryo-fetal malformations at maternal exposures (AUC) approximately ≥3-(rat) and ≥0.07 (rabbit) times the human exposure (AUC) at the recommended dose (see Animal Data). Advise pregnant women and females of reproductive potential of the potential risk to the fetus.

In the U.S. general population, the estimated background risk of major birth defects and miscarriage in clinically recognized pregnancies is 2 to 4% and 15 to 20%, respectively.

Data

Animal Data

Embryo-fetal development studies were conducted in rats with administration of belumosudil to pregnant animals during the period of organogenesis at oral doses of 25, 50, 150, and 300 mg/kg/day in a pilot study and doses of 15, 50, and 150 mg/kg/day in a pivotal study. In the pilot study, maternal toxicity and embryo-fetal developmental effects were observed. Maternal toxicity (reduced body weight gain) occurred at 150 and 300 mg/kg/day doses. Increased post-implantation loss occurred at 50 and 300 mg/kg/day. Fetal-malformations were observed at ≥50 mg/kg/day and included absence of anus and tail, omphalocele, and dome shaped head. The exposure (AUC) at 50 mg/kg/day in rats is approximately 3 times the human exposure at the recommended dose of 200 mg.

In an embryo-fetal developmental study in rabbits, pregnant animals administered oral doses of belumosudil at 50, 125, and 225 mg/kg/day during the period of organogenesis resulted in maternal toxicity and embryo-fetal developmental effects. Maternal toxicity (body weight loss and mortality) was observed at doses≥125 mg/kg/day. Embryo-fetal effects were observed at doses≥50 mg/kg/day and included spontaneous abortion, increased post-implantation loss, decreased percentage of live fetuses, malformations, and decreased fetal body weight. Malformations included those in the tail (short), ribs (branched, fused or deformed), sternebrae (fused), and neural arches (fused, misaligned, and deformed). The exposure (AUC) at 50 mg/kg/day in rabbits is approximately 0.07 times the human exposure at the recommended dose of 200 mg.

8.2 Lactation
Risk Summary

There are no data available on the presence of belumosudil or its metabolites in human milk or the effects on the breastfed child, or milk production. Because of the potential for serious adverse reactions from belumosudil in the breastfed child, advise lactating women not to breastfeed during treatment with REZUROCK and for at least one week after the last dose.

8.3 Females and Males of Reproductive Potential

REZUROCK can cause fetal harm when administered to a pregnant woman [see Use in Specific Populations (8.1)].
Pregnancy Testing Verify the pregnancy status of females of reproductive potential prior to initiating treatment with REZUROCK.
Contraception
Females Advise females of reproductive potential to use effective contraception during treatment with REZUROCK and for at least one week after the last dose of REZUROCK. If this drug is used during pregnancy or if the patient becomes pregnant while taking this drug, the patient should be informed of the potential hazard to a fetus.
Males Advise males with female partners of reproductive potential to use effective contraception during treatment with REZUROCK and for at least one week after the last dose of REZUROCK.
Infertility
Females Based on findings from rats, REZUROCK may impair female fertility. The effect on fertility is reversible [see Nonclinical Toxicology (13.1)].
Males Based on findings from rats and dogs, REZUROCK may impair male fertility. The effects on fertility are reversible [see Nonclinical Toxicology (13.1)].

8.4 Pediatric Use

The safety and effectiveness of REZUROCK have been established in pediatric patients 12 years and older. Use of REZUROCK in this age group is supported by evidence from adequate and well-controlled studies of REZUROCK in adults with additional population pharmacokinetic data demonstrating that age and body weight had no clinically meaningful effect on the pharmacokinetics of drug substance, that the exposure of drug substance is expected to be similar between adults and pediatric patients age 12 years and older, and that the course of disease is sufficiently similar in adult and pediatric patients to allow extrapolation of data in adults to pediatric patients.

The safety and effectiveness of REZUROCK in pediatric patients less than 12 years old have not been established.

8.5 Geriatric Use

Of the 186 patients with chronic GVHD in clinical studies of REZUROCK, 26% were years and older. No clinically meaningful differences in safety or effectiveness of REZUROCK were observed in comparison to younger patients.

11 Description

Belumosudil is a kinase inhibitor. The active pharmaceutical ingredient is belumosudil mesylate with the molecular formula $C_{27}H_{28}N_6O_5S$ and the molecular weight is 548.62 g/mol. The chemical name for belumosudil mesylate is 2-{3-[4-(1H-indazol-5-ylamino)-2-quinazolinyl]phenoxy}-N-(propan-2-yl) acetamide methanesulfonate (1:1). The chemical structure is as follows:

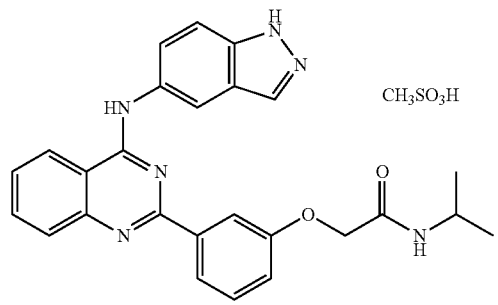

Belumosudil mesylate is a yellow powder that is practically insoluble in water, slightly soluble in methanol and DMF and soluble in DMSO.

REZUROCK tablets are for oral administration. Each tablet contains 200 mg of the free base equivalent to 242.5 mg of belumosudil mesylate. The tablet also contains the following inactive ingredients: microcrystalline cellulose, hypromellose, croscarmellose sodium, colloidal silicon dioxide, and magnesium stearate.

The tablet film consists of polyvinyl alcohol, polyethylene glycol, talc, titanium dioxide and yellow iron oxide.

12 Clinical Pharmacology 12.1 Mechanism of Action

Belumosudil is an inhibitor of rho-associated, coiled-coil containing protein kinase (ROCK) which inhibits ROCK2 and ROCK1 with $IC_{50}$ values of approximately 100 nM and 3 µM, respectively. Belumosudil down-regulated proinflammatory responses via regulation of STAT3/STAT5 phosphorylation and shifting Th17/Treg balance in ex-vivo or in vitro-human T cell assays. Belumosudil also inhibited aberrant pro-fibrotic signaling, in vitro. In vivo, belumosudil demonstrated activity in animal models of chronic GVHD.

12.2 Pharmacodynamics

Belumosudil exposure-response relationships and the time course of pharmacodynamic response are not established.

12.3 Pharmacokinetics

The following pharmacokinetic parameters are presented for chronic GVHD patients administered belumosudil 200 mg once daily, unless otherwise specified. The mean (% coefficient of variation, % CV) steady-state AUC and $C_{max}$ of belumosudil was 22700 (48%) h·ng/mL and 2390 (44%) ng/mL, respectively. Belumosudil $C_{max}$ and AUC increased in an approximately proportional manner over a dosage range of 200 and 400 mg (1 to 2 times once daily recommended dosage). The accumulation ratio of belumosudil was 1.4.

Absorption

Median $T_{max}$ of belumosudil at steady state was 1.26 to 2.53 hours following administration of 200 mg once daily or twice daily in patients. The mean (% CV) bioavailability was 64% (17%) following a single belumosudil dose in healthy subjects.

Effect of Food

Belumosudil $C_{max}$ and AUC increased 2.2 times and 2 times, respectively, following administration of a single belumosudil dose with a high-fat and high-calorie meal (800 to 1,000 calories with approximately 50% of total caloric content of the meal from fat) compared to the fasted state in healthy subjects. Median $T_{max}$ was delayed 0.5 hours.

Distribution

The geometric mean volume of distribution after a single dose of belumosudil in healthy subjects was 184 L (geo CV % 67.7%).

Belumosudil binding to human serum albumin and human α1-acid glycoprotein was 99.9% and 98.6%, respectively, in vitro.

Elimination

The mean (% CV) elimination half-life of belumosudil was 19 hours (39%), and clearance was 9.83 L/hours (46%) in patients.

Metabolism

Belumosudil is primarily metabolized by CYP3A4 and to a lesser extent by CYP2C8, CYP2D6, and UGT1A9, in vitro.

Excretion

Following a single oral dose of radiolabeled belumosudil in healthy subjects, 85% of radioactivity was recovered in feces (30% as unchanged) and less than 5% in urine.

Specific Populations

No clinically significant differences in belumosudil pharmacokinetics were observed with regard to age (18 to 77 years), sex, weight (38.6 to 143 kg), or mild to moderate renal impairment (eGFR≥60 and <90 mL/min/1.72m 2 to eGFR≥30 and <60 mL/min/1.72m 2). The effect of severe renal impairment on the pharmacokinetics of belumosudil has not been studied.

Drug Interaction Studies

Clinical Studies and Model-Informed Approaches Effects of Other Drugs on Belumosudil Strong Cytochrome P450 (CYP) 3A Inhibitors: There was no clinically meaningful effect on belumosudil exposure when coadministered with itraconazole in healthy subjects.

Strong CYP3A Inducers: Coadministration of rifampin decreased belumosudil $C_{max}$ by 59% and AUC by 72% in healthy subjects.

Moderate CYP3A Inducers: Coadministration of efavirenz is predicted to decrease belumosudil $C_{max}$ by 32% and AUC by 35% in healthy subjects.

Proton Pump Inhibitors: Coadministration of rabeprazole decreased belumosudil $C_{max}$ by 87% and AUC by 80%, and omeprazole decreased belumosudil $C_{max}$ by 68% and AUC by 47% in healthy subjects.

Effects of Belumosudil on Other Drugs

CYP3A Substrates: Coadministration of belumosudil is predicted to increase midazolam (a sensitive CYP3A substrate) $C_{max}$ and AUC approximately 1.3- and 1.5-fold, respectively.

CYP2C9 Substrates: Coadministration of belumosudil is not expected to have clinically meaningful effect on the exposure of CYP2C9 substrates (such as warfarin).

CYP2C8 Substrates: Coadministration of belumosudil is not expected to have clinically meaningful effect on the exposure of CYP2C8 substrates that are not an OATP1B1 substrate.

In Vitro Studies

Transporter Systems: Belumosudil is a substrate of P-gp. Belumosudil inhibits BCRP, P-gp, and OATP1B1 at clinically relevant concentrations.

Enzymes Systems: Belumosudil is an inhibitor of CYP1A2, CYP2C19, CYP2D6, UGT1A1 and UGT1A9.

13 Nonclinical Toxicology 13.1 Carcinogenesis, Mutagenesis, Impairment of Fertility Carcinogenicity studies have not been conducted with belumosudil.

Belumosudil was not genotoxic in an in vitro bacterial mutagenicity (Ames) assay, in vitro chromosome aberration assay in human peripheral blood lymphocytes (HPBL) or an in vivo rat bone marrow micronucleus assay.

In a combined male and female rat fertility study, belumosudil-treated male animals were mated with untreated females, or untreated males were mated with belumosudil-treated females. Belumosudil was administered orally at doses of 50, 150 or 275 mg/kg/day to male rats 70 days prior to and throughout the mating period, and to female rats 14 days prior to mating and up to Gestation Day 7. At the dose of 275 mg/kg/day, adverse findings in female rats (treated with belumosudil or untreated but mated with treated males) included increased pre- or post-implantation loss and decreased number of viable embryos. Administration of belumosudil to male rats at a dose of 275 mg/kg/day resulted in abnormal sperm findings (reduced motility, reduced count, and increased percentage of abnormal sperm), and testes/epididymis organ changes (reduced weight and degeneration).

Fertility was reduced in both treated males or females at the 275 mg/kg/day dose and reached statistical significance in males. Adverse changes in male and female reproductive organs also occurred in general toxicology studies; findings included spermatozoa degeneration at a belumosudil dose of 35 mg/kg/day in dogs and decreased follicular development in ovaries at 275 mg/kg/day in rats. Changes were partially or fully reversed during the recovery period. The exposure (AUC) at the doses of 35 mg/kg/day in dogs, and 275 mg/kg/day in rats is 0.5 times and 8-9 times, respectively, the clinical exposure at the recommended dose of 200 mg daily.

14 Clinical Studies 14.1 Chronic Graft versus Host Disease

Study KD025-213 (NCT03640481) was a randomized, open-label, multicenter study of REZUROCK for treatment of patients with chronic GVHD who had received 2 to 5 prior lines of systemic therapy and required additional treatment. Patients were excluded from the studies if platelets were <50×10$^9$/L; absolute neutrophil count<1.5×10$^9$/L; AST or ALT>3×ULN; total bilirubin>1.5×ULN; QTc(F) >480 ms; eGFR<30 mL/min/1.73 m$^2$; or FEV1≤39%. There were 66 patients treated with REZUROCK 200 mg taken orally once daily. Concomitant treatment with supportive care therapies for chronic GVHD was permitted. Concomitant treatment with GVHD prophylaxis and standard care systemic chronic GVHD therapies was permitted as long as the subject has been on a stable dose for at least 2 weeks prior to study. Initiation of new systemic chronic GVHD therapy while on study was not permitted.

Demographics and baseline characteristics are summarized in Table 15.

TABLE 15

Demographics and Baseline Characteristics of Patients with Chronic GVHD

| | REZUROCK 200 mg once daily (N = 65) |
|---|---|
| Age, Median, Years (minimum, maximum) | 53 (21, 77) |
| Age ≥65 Years, n (%) | 17 (26) |
| Male, n (%) | 42 (65) |
| Race, n (%) | |
| White | 54 (83) |
| Black | 6 (9) |
| Other or Not Reported | 5 (8) |
| Median (range) time (months) from Chronic GVHD Diagnosis | 25.3 (1.9, 162.4) |
| ≥4 Organs Involved, n (%) | 31 (48) |
| Median (range) Number of Prior Lines of Therapy | 3 (2, 6) |
| Number of Prior Lines of Therapy, n (%) | |
| 2 | 23 (35) |
| 3 | 12 (19) |
| 4 | 15 (23) |
| ≥5 | 15 (23) |
| Prior chronic GVHD treatment with ibrutinib, n (%) | 21 (32) |
| Prior chronic GVHD treatment with ruxolitinib, n (%) | 20 (31) |
| Refractory to Last Therapy, n (%$^a$) | 43/55 (78) |
| Severe chronic GVHD, n (%) | 46 (71) |
| Median (range) Global Severity Rating | 7 (2, 9) |
| Median (range) Lee Symptom Scale Score at baseline | 27 (7, 56) |
| Median (range) Corticosteroid dose at baseline (PE/kg)$^b$ | 0.19 (0.03, 0.95) |

$^a$Denominator excludes patients with unknown status
$^b$Prednisone equivalents/kilogram The efficacy of REZUROCK was based on overall response rate (ORR) through Cycle 7 Day 1 where overall response included complete response or partial response according to the 2014 NIH Response Criteria. The ORR results are presented in Table 16. The ORR was 75% (95% CI: 63, 85). The median duration of response, calculated from first response to progression, death, or new systemic therapies for chronic GVHD, was 1.9 months (95% CI: 1.2, 2.9). The median time to first response was 1.8 months (95% CI: 1.0, 1.9). In patients who achieved response, no death or new systemic therapy initiation occurred in 62% (95% CI: 46, 74) of patients for at least 12 months since response.

TABLE 16

Overall Response Rate through Cycle 7 Day 1 for Patients with Chronic GVHD in Study KD025-213

| | REZUROCK 200 mg once daily (N = 65) |
|---|---|
| Overall Response Rate (ORR) | 49 (75%) |
| 95% Confidence Interval$^a$ | (63%, 85%) |
| Complete Response | 4 (6%) |
| Partial Response | 45 (69%) |

$^a$Estimated using Clopper-Pearson method

ORR results were supported by exploratory analyses of patient-reported symptom bother which showed at least a 7-point decrease in the Lee Symptom Scale summary score through Cycle 7 Day 1 in 52% (95% CI: 40, 65) of patients.

16 How Supplied/Storage and Handling

REZUROCK 200 mg tablets are supplied as pale yellow film-coated oblong tablets containing 200 mg of belumosudil (equivalent to 242.5 mg belumosudil mesylate). Each tablet is debossed with "KDM" on one side and "200" on the other side and is packaged as follows:

200 mg tablets in 30 count bottle: NDC 79802-200-30

Store at room temperature, 20° C. to 25° C. (68° F. to 77° F.); excursions permitted from and 30° C. (59° F. to 86° F.) [see USP Controlled Room Temperature].

Dispense to patient in original container only. Store in original container to protect from moisture. Replace cap securely each time after opening. Do not discard desiccant.

17 Patient Counseling Information

Advise the patient to read the FDA-approved patient labeling (Patient Information).

Embryo-Fetal Toxicity:

Advise pregnant women and females of reproductive potential of the potential risk to a fetus. Advise females of reproductive potential to inform their healthcare provider of a known or suspected pregnancy [see Warnings and Precautions (5.1), Use in Specific Populations (8.1, 8.3)].

Advise females of reproductive potential to use effective contraceptive during treatment with REZUROCK and for at least one week after the last dose [see Warnings and Precautions (5.1)].

Advise males with female partners of reproductive potential to use effective contraceptive during treatment with REZUROCK and for at least one week after the last dose [see Use in Specific Populations (8.3)].

Lactation

Advise women not to breastfeed during treatment with REZUROCK and for at least one week after the last dose [see Use in Specific Populations (8.2)].

Infertility

Advise males and females of reproductive potential that REZUROCK may impair fertility [see Use in Specific Populations (8.3)].

Administration

Inform patients to take REZUROCK orally once daily with food according to their physician's instructions and that the oral dosage (tablets) should be swallowed whole with a glass of water without cutting, crushing or chewing the tablets approximately the same time each day [see Dosage and Administration (2.1)].

Advise patients that in the event of a missed daily dose of REZUROCK, it should be taken as soon as possible on the same day with a return to the normal schedule the following day. Patients should not take extra doses to make up the missed dose [see Dosage and Administration (2.1)].

Drug Interactions

Advise patients to inform their health care providers of all concomitant medications, including prescription medicines, over-the-counter drugs, vitamins, and herbal products [see Drug Interactions (7)]

PATIENT INFORMATION
REZUROCK (REZ-ur-ok)
(belumosudil)
tablets

What is REZUROCK?
REZUROCK is a prescription medicine used to treat adults and children 12 years of age and older with chronic graft-versus-host disease (chronic GVHD) after you have received at least 2 prior treatments (systemic therapy) and they did
not work.
It is not known if REZUROCK is safe and effective in children less than 12 years old.
Before taking REZUROCK, tell your healthcare provider about all of your medical conditions, including if you:
have kidney or liver problems.
are pregnant or plan to become pregnant. REZUROCK can harm your unborn baby. If you are able to become
pregnant, your healthcare provider will do a pregnancy test before starting treatment with REZUROCK. Tell your
healthcare provider if you become pregnant or think you may be pregnant during treatment with REZUROCK.
Females who can become pregnant should use effective birth control during treatment with REZUROCK and
for at least 1 week after the last dose.
Males with female partners who can become pregnant should use effective birth control during treatment with
REZUROCK and for at least 1 week after the last dose.
are breastfeeding or plan to breastfeed. It is not known if REZUROCK passes into breast milk. Do not breastfeed
during treatment with REZUROCK and for at least 1 week after the last dose.
Tell your healthcare provider about all the medicines you take, including prescription and over-the-counter
medicines, vitamins, and herbal supplements. REZUROCK may affect the way other medicines work, and other
medicines may affect the way REZUROCK works.
Know the medicines you take. Keep a list of them to show your healthcare provider and pharmacist when you get a
new medicine.
How should I take REZUROCK?
Take REZUROCK exactly as your healthcare provider tells you to take it.
Do not change your dose or stop taking REZUROCK without first talking to your healthcare provider.
Take REZUROCK 1 time a day with a meal.
Take REZUROCK at about the same time each day.
Swallow REZUROCK tablets whole with a glass of water.
Do not cut, crush, or chew REZUROCK tablets.
Your healthcare provider will do blood tests to check your liver at least 1 time a month during treatment with
REZUROCK.
If you miss a dose of REZUROCK, take it as soon as you remember on the same day. Take your next dose of
REZUROCK at your regular time on the next day. Do not take extra doses of REZUROCK to make up for a missed
dose.
If you take too much REZUROCK, call your healthcare provider or go to the nearest hospital emergency room right
away.
What are the possible side effects of REZUROCK?
The most common side effects of REZUROCK include:

| | |
|---|---|
| infections | swelling |
| tiredness or weakness | bleeding |
| nausea | stomach (abdominal) pain |
| diarrhea | muscle or bone pain |
| shortness of breath | headache |
| cough | high blood pressure |

Your healthcare provider may change your dose of REZUROCK, temporarily stop, or permanently stop
treatment with REZUROCK if you have certain side effects.
REZUROCK may affect fertility in males and females. Talk to your healthcare provider if this is a concern for you.
These are not all the possible side effects of REZUROCK.
Call your doctor for medical advice about side effects. You may report side effects to FDA at 1-800-FDA-1088. You
may also report side effects to Kadmon Pharmaceuticals, LLC at 1-877-377-7862.
How should I store REZUROCK?
Store REZUROCK at room temperature between 68° F. to 77° F. (20° C. to 25° C.).
Keep REZUROCK in its original container. The REZUROCK bottle contains a desiccant packet to help keep your
tablets dry (protect from moisture). Keep the desiccant in the bottle.
Tightly close the REZUROCK bottle after you take your dose.
Keep REZUROCK and all medicines out of the reach of children.
General information about the safe and effective use of REZUROCK.
Medicines are sometimes prescribed for purposes other than those listed in a Patient
Information leaflet. Do not use REZUROCK for a condition for which it was not
prescribed. Do not give REZUROCK to other people, even if they have
the same symptoms that you have. It may harm them. You can ask your pharmacist or
healthcare provider for information about REZUROCK that is written for health
professionals.
What are the ingredients in REZUROCK?
Active ingredient:
belumosudil mesylate
Inactive ingredients:
Tablet core: microcrystalline cellulose, hypromellose, croscarmellose sodium, colloidal
silicon dioxide, and magnesium stearate.
Tablet coating: polyvinyl alcohol, polyethylene glycol, talc, titanium dioxide and yellow
iron oxide.

Although the present invention has been described in some detail by way of illustration and example for purposes of clarity and understanding, the descriptions and examples should not be construed as limiting the scope of the invention. The disclosures of all patent and scientific literature cited herein are expressly incorporated herein in their entirety by reference.

The invention claimed is:

1. A method of treating chronic graft-versus-host disease (cGVHD) in a patient in need thereof comprising the steps of:
   (a) administering 2-{3-[4-(1H-indazol-5-ylamino)-2-quinazolinyl]phenoxy}-N-(propan-2-yl) acetamide, or a pharmaceutically acceptable salt thereof (Compound) to the patient at a daily dose that is equivalent to 200 mg of the free base of the Compound;
   (b) identifying an adverse reaction in the patient, wherein the adverse reaction is an infection;
   (c) ceasing administration of the Compound to the patient when the adverse reaction is an infection at a Grade 3 level; wherein an infection at a Grade 3 level comprises an infection wherein intravenous (IV) antibiotic, antifungal, antiviral, radiological or operative intervention is indicated; and
   (d) resuming administration of the Compound to the patient at the previously administered daily dose when the patient's infection has recovered to Grade 1 level or less, wherein an infection at a Grade 1 level comprises an infection wherein intervention is not indicated.

2. A method of treating chronic graft-versus-host disease (cGVHD) in a patient in need thereof comprising the steps of:
   (a) administering 2-{3-[4-(1H-indazol-5-ylamino)-2-quinazolinyl]phenoxy}-N-(propan-2-yl) acetamide, or a pharmaceutically acceptable salt thereof (Compound) to the patient at a daily dose that is equivalent to 200 mg of the free base of the Compound;
   (b) identifying an adverse reaction in the patient, wherein the adverse reaction is an infection;
   (c) permanently ceasing administration of the Compound to the patient when the patient's adverse reaction comprises a Grade 4 level infection, wherein a Grade 4 level infection comprises an infection that is life-threatening and wherein urgent intervention is indicated.

3. The method according to claim 1, wherein the Compound is belumosudil mesylate salt.

4. The method according to claim 1, wherein the patient has failed at least two prior lines of systemic therapy for the cGVHD.

5. The method according to claim 2, wherein the Compound is belumosudil mesylate salt.

6. The method according to claim 2, wherein the patient has failed at least two prior lines of systemic therapy for the cGVHD.

* * * * *

(12) EX PARTE REEXAMINATION CERTIFICATE (264th)
Ex Parte Reexamination Ordered under 35 U.S.C. 257

United States Patent
Eiznhamer et al.

(10) Number: US 12,097,202 C1
(45) Certificate Issued: Jan. 30, 2026

(54) METHODS OF ADMINISTERING BELUMOSUDIL FOR TREATMENT OF CHRONIC GRAFT VERSUS HOST DISEASE

(71) Applicant: Kadmon Corporation, LLC, Bridgewater, NJ (US)

(72) Inventors: David Eiznhamer, Cambridge, MA (US); Heidi Krenz, Cambridge, MA (US)

(73) Assignee: KADMON CORPORATION, LLC, Bridgewater, NJ (US)

Supplemental Examination Request:
No. 96/050,091, May 7, 2025

Reexamination Certificate for:
Patent No.: 12,097,202
Issued: Sep. 24, 2024
Appl. No.: 18/105,285
Filed: Feb. 3, 2023

Related U.S. Application Data

(63) Continuation of application No. PCT/US2022/037207, filed on Jul. 14, 2022.

(51) Int. Cl.
*A61K 31/517* (2006.01)
*A61K 9/20* (2006.01)
*A61P 37/06* (2006.01)

(52) U.S. Cl.
CPC .......... *A61K 31/517* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61P 37/06* (2018.01)

(58) Field of Classification Search
None
See application file for complete search history.

(56) References Cited

To view the complete listing of prior art documents cited during the supplemental examination proceeding and the resulting reexamination proceeding for Control Number 96/050,091, please refer to the USPTO's Patent Electronic System.

*Primary Examiner* — Joseph R Kosack

(57) ABSTRACT

The present disclosure provides methods of administering belumosudil mesylate salt to patients with chronic graft-versus-host disease (cGVHD), wherein the methods include identifying adverse reactions in the patients, such as an infection, and modifying the administration based on the results of such identification, such as by ceasing administration when the infection is a Grade 3 or Grade 4 level infection.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 5-6 were previously disclaimed.

Claim 1 is determined to be patentable as amended.

Claims 3 and 4, dependent on an amended claim, are determined to be patentable.

1. A method of treating chronic graft-versus-host disease (cGVHD) in a patient in need thereof comprising the steps of:
   (a) administering 2-{3-[4-(1H-indazol-5-ylamino)-2-quinazolinyl] phenoxy}-N-(propan-2-yl) acetamide, or a pharmaceutically acceptable salt thereof (Compound) to the patient at a daily dose that is equivalent to 200 mg of the free base of the Compound;
   (b) identifying an adverse reaction in the patient, wherein the adverse reaction is [an] *a treatment-related* infection;
   (c) ceasing administration of the Compound to the patient when the adverse reaction is an infection at a Grade 3 level; wherein [an] *a treatment-related* infection at a Grade 3 level comprises an infection wherein intravenous (IV) antibiotic, antifungal, antiviral, radiological or operative intervention is indicated; and
   (d) resuming administration of the Compound to the patient at the previously administered daily dose when the patient's *treatment-related* infection has recovered to Grade 1 level or less, wherein an infection at a Grade 1 level comprises an infection wherein intervention is not indicated.

\* \* \* \* \*